(12) United States Patent
Tabuteau

(10) Patent No.: US 9,127,069 B1
(45) Date of Patent: Sep. 8, 2015

(54) COMPOSITIONS COMPRISING RANK/RANKL ANTAGONISTS AND RELATED COMPOUNDS FOR TREATING PAIN

(71) Applicant: Antecip Bioventures LLC, New York, NY (US)

(72) Inventor: Herriot Tabuteau, New York, NY (US)

(73) Assignee: Antecip Bioventures LLC, New York, NY (US)

( * ) Notice: Subject to any disclaimer, the term of this patent is extended or adjusted under 35 U.S.C. 154(b) by 0 days.

(21) Appl. No.: 14/495,732

(22) Filed: Sep. 24, 2014

Related U.S. Application Data

(60) Provisional application No. 62/012,112, filed on Jun. 13, 2014, provisional application No. 62/010,754, filed on Jun. 11, 2014.

(51) Int. Cl.
| | | |
|---|---|---|
| *A61K 39/395* | (2006.01) | |
| *C07K 16/28* | (2006.01) | |
| *A61K 45/06* | (2006.01) | |
| *C07K 16/24* | (2006.01) | |
| *A61K 39/00* | (2006.01) | |

(52) U.S. Cl.
CPC ......... *C07K 16/2878* (2013.01); *A61K 39/3955* (2013.01); *A61K 45/06* (2013.01); *C07K 16/241* (2013.01); *A61K 2039/505* (2013.01); *C07K 2317/30* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 8,802,658 B2 | 8/2014 | Tabuteau | |
| 8,822,436 B1 | 9/2014 | Tabuteau | |
| 8,835,650 B1 | 9/2014 | Tabuteau | |
| 8,859,530 B2 | 10/2014 | Desai | |
| 8,865,757 B1 | 10/2014 | Tabuteau | |
| 8,901,161 B1 | 12/2014 | Tabuteau | |
| 8,901,162 B1 | 12/2014 | Tabuteau | |
| 8,901,962 B2 | 12/2014 | Norman | |
| 2004/0063670 A1 | 4/2004 | Fox et al. | |
| 2010/0215743 A1 | 8/2010 | Leonard | |
| 2011/0028435 A1 | 2/2011 | Hanna et al. | |
| 2011/0098252 A1 | 4/2011 | Pappagallo | |
| 2012/0190647 A1 | 7/2012 | Hanna et al. | |
| 2013/0274282 A1 | 10/2013 | Tabuteau | |
| 2013/0303485 A1 | 11/2013 | Tabuteau | |
| 2013/0303486 A1 | 11/2013 | Tabuteau | |
| 2013/0303487 A1 | 11/2013 | Tabuteau | |
| 2013/0303488 A1 | 11/2013 | Tabuteau | |
| 2014/0051669 A1 | 2/2014 | Tabuteau | |
| 2014/0051718 A1 | 2/2014 | Tabuteau | |
| 2014/0107345 A1 | 4/2014 | Tabuteau | |
| 2014/0249107 A1 | 9/2014 | Tabuteau | |
| 2014/0249108 A1 | 9/2014 | Tabuteau | |
| 2014/0249109 A1 | 9/2014 | Tabuteau | |
| 2014/0249110 A1 | 9/2014 | Tabuteau | |
| 2014/0249111 A1 | 9/2014 | Tabuteau | |
| 2014/0249112 A1 | 9/2014 | Tabuteau | |
| 2014/0249113 A1 | 9/2014 | Tabuteau | |
| 2014/0249317 A1 | 9/2014 | Tabuteau | |
| 2014/0256683 A1 | 9/2014 | Tabuteau | |
| 2014/0329773 A1 | 11/2014 | Tabuteau | |
| 2014/0348916 A1 | 11/2014 | Tabuteau | |
| 2014/0349974 A1 | 11/2014 | Tabuteau | |

FOREIGN PATENT DOCUMENTS

| | | |
|---|---|---|
| WO | 02087555 | 11/2002 |
| WO | 2005063218 | 7/2005 |
| WO | 2005/107751 A1 | 11/2005 |
| WO | 2012071517 | 5/2012 |

OTHER PUBLICATIONS

Ohba et al. (2014). Bone. 63:110-120.*
Lin et al. (2010). Brain Research Bulletin. 83:284-291.*
Roudier et al. (2006). Clin. Exp. Metastasis. 23:167-175.*
Luger et al. (2001) Cancer Research. 61:4038-4047.*
Rasulova et al. (2013) World Journal of Nuclear Medicine 12(1):19-23.*
U.S. Appl. No. 14/495,732, filed Jan. 26, 2015, First Named Inventor: Herriot Tabuteau, Assignee: Antecip Bioventures II LLC.
U.S. Appl. No. 14/481,097, filed Sep. 9, 2014, First Named Inventor: Herriot Tabuteau Assignee: Antecip Bioventures II LLC.
U.S. Appl. No. 14/538,709, filed Nov. 11, 2014, First Named Inventor: Herriot Tabuteau Assignee: Antecip Bioventures II LLC.
U.S. Appl. No. 14/530,556, filed Oct. 31, 2014, First Named Inventor: Herriot Tabuteau Assignee: Antecip Bioventures II LLC.
U.S. Appl. No. 14/536,526, filed Jan. 28, 2015, First Named Inventor: Herriot Tabuteau Assignee: Antecip Bioventures II LLC.
U.S. Appl. No. 14/540,333, filed Nov. 13, 2014, First Named Inventor: Herriot Tabuteau Assignee: Antecip Bioventures II LLC.
U.S. Appl. No. 14/604,524, filed Jan. 23, 2015, First Named Inventor: Herriot Tabuteau Assignee: Antecip Bioventures II LLC.
U.S. Appl. No. 14/605,822, filed Jan. 26, 2015, First Named Inventor: Herriot Tabuteau Assignee: Antecip Bioventures II LLC.
U.S. Appl. No. 14/607,947, filed Jan. 28, 2015, First Named Inventor: Herriot Tabuteau Assignee: Antecip Bioventures II LLC.
U.S. Appl. No. 14/607,985, filed Jan. 28, 2015, First Named Inventor: Herriot Tabuteau Assignee: Antecip Bioventures II LLC.
U.S. Appl. No. 13/894,244, filed May 14, 2013, First Named Inventor: Herriot Tabuteau, Assignee: Antecip Bioventures II LLC.
U.S. Appl. No. 13/894,252, filed May 14, 2013, First Named Inventor: Herriot Tabuteau Assignee: Antecip Bioventures II LLC.
U.S. Appl. No. 13/894,262, filed May 14, 2013, First Named Inventor: Herriot Tabuteau Assignee: Antecip Bioventures II LLC.

(Continued)

*Primary Examiner* — Christine J Saoud
*Assistant Examiner* — Jon M Lockard
(74) *Attorney, Agent, or Firm* — K&L Gates LLP; Louis C. Cullman; Brent A. Johnson

(57) ABSTRACT

Disclosed herein are method of treating pain using comprising RANK/RANKL antagonists.

20 Claims, 5 Drawing Sheets

(56) References Cited

OTHER PUBLICATIONS

U.S. Appl. No. 13/894,274, filed May 14, 2013, First Named Inventor: Herriot Tabuteau Assignee: Antecip Bioventures II LLC.
U.S. Appl. No. 14/106,291, filed Dec. 13, 2013, First Named Inventor: Herriot Tabuteau Assignee: Antecip Bioventures II LLC.
U.S. Appl. No. 14/279,196, filed May 15, 2014, First Named Inventor: Herriot Tabuteau Assignee: Antecip Bioventures II LLC.
U.S. Appl. No. 14/279,206, filed May 15, 2014 First Named Inventor: Herriot Tabuteau Assignee: Antecip Bioventures II LLC.
U.S. Appl. No. 14/279,213, filed May 15, 2014, First Named Inventor: Herriot Tabuteau Assignee: Antecip Bioventures II LLC.
U.S. Appl. No. 14/279,222, filed May 15, 2014, First Named Inventor: Herriot Tabuteau Assignee: Antecip Bioventures II LLC.
U.S. Appl. No. 14/279,226, filed May 15, 2014, First Named Inventor: Herriot Tabuteau Assignee: Antecip Bioventures II LLC.
U.S. Appl. No. 14/279,229, filed May 15, 2014 First Named Inventor: Herriot Tabuteau Assignee: Antecip Bioventures II LLC.
U.S. Appl. No. 14/279,232, filed May 15, 2014, First Named Inventor: Herriot Tabuteau Assignee: Antecip Bioventures II LLC.
U.S. Appl. No. 14/279,241, filed May 15, 2014 First Named Inventor: Herriot Tabuteau Assignee: Antecip Bioventures II LLC.
U.S. Appl. No. 14/279,236, filed May 15, 2014, First Named Inventor: Herriot Tabuteau Assignee: Antecip Bioventures II LLC.
U.S. Appl. No. 14/336,642, filed Jul. 21, 2014, First Named Inventor: Herriot Tabuteau Assignee: Antecip Bioventures II LLC.
U.S. Appl. No. 14/456,939, filed Aug. 11, 2014, First Named Inventor: Herriot Tabuteau Assignee: Antecip Bioventures II LLC.
U.S. Appl. No. 14/457,659, filed Aug. 12, 2014, First Named Inventor: Herriot Tabuteau Assignee: Antecip Bioventures II LLC.
Chandler, Labeling of unit dose packages of drugs, Department of Pharmacy Policy, University of Kentucky Hospital, Chandler Medical Center, policy No. PH-04-06, 2009 (cited by examiner in co-pending application 13/894,244).
Committee for Orphan Medicinal Products (COMP) meeting report on the review of applications for orphan designation, European Medicines Agency, Sep. 2013.
Conte, et al., The Oncologist 2004:9(Supp 4):28-37.
English, A life of pain: woman chooses amputation to deal with painful disorder. Http://www.katu.com/news/loca.A-life-of-pain-woman-chooses amputation-to-deal with . . . Nov. 18, 2013.
Opinion of the Committee for Orphan Medicinal Products on orphan medicinal product designation, European Medicines Agency, Sep. 2013, pp. 1-3.
Sebastian, Complex regional pain syndrome. Indian J. Past Surg., 44(2): 298-307 (2011).
The University of Sheffield, Health & Economic impact of a new drug intervention for osteoporosis. http://www.sheffield.ac.uk/humanmetabolism/researchandyou/zoledronicacid, accessed Jun. 2014.
US Product Label for Zometa, revised 2012, Prescribing info.
U.S. Appl. No. 14/625,457, filed Feb. 18, 2015 First Named Inventor: Herriot Tabuteau Assignee: Antecip Bioventures II LLC.
ISR & Written Opinion for PCT/US2014/050427, mailed Nov. 20, 2014.
Bertorelli et al., Nociceptin and the ORL-1 ligand [Phe1(CH2-NH)Gly2]nociceptin(1-13)NH2 exert anti-opioid effects in the Freund's adjuvant-induced arthritic rat model of chronic pain. British Journal of Pharmacology (1999) 128, 1252-1258.
Bingham III et al., Risedronate decreases biochemical markers of cartilage degradation but does not decrease symptoms or slow radiographic progression in patients with medical compartment osteoarthritis of the knee. Arthritis & Rheumatism, vol. 54, No. 11, 2006, 3494-3507.
Cullen et al., MER-101: A bioavailability study of various GIPET formulations in beagle dogs with intraduodenal cannulae. Poster Presentation, Nov. 2007.
De Castro et al., Zoledronic acid to treat complex regional pain syndrome type I in adult (case report). Rev. Dor. Sao Paulo, 2011, 12(1): 71-73.
EU Product Label for Zometa, accessed 2013.
Giles, Risedronate not an Effective Disease Modifier in Knee Osteoarthritis. Arthritis News (website) 2006. Accessed at http://www.hopkinsarthritis.orgiarthritis-news/risedronate-not-an-effective-disease-modifier-in-knee-osteoarthritis.
Guo et al., Substance P signaling contributes to the vascular and nociceptive abnormalities observed in a tibial fracture rat model of complex regional pain syndrome type I. Pain 108 (2004) 95-107.
Kingery et al., A substance P receptor (NK1) antagonist can reverse vascular and nociceptive abnormalities in a rat model of complex regional pain syndrome type II. Pain 104 (2003) 75-84.
Laslett, Extended report: Zoledronic acid reduces knee pain and bone marrow lesions over 1 year: a randomized controlled trial. Ann. Rheum. Dis. 2012, 71: 1322-1328.
Leonard et al., MER-101 Tablets: A pilot bioavailability study of a novel oral formulation of zoledronic acid. Poster Presentation, Oct. 2007.
Leonard et al., Safety Profile of Zoledronic acid in a novel oral formulation. Poster Presentation, Nov. 2009.
Leonard et al., Studies of bioavailability and food effects of MER-101 Zoledronic Acid Tablets in Postmenopausal Women. Poster Presentation, Oct. 2009.
McHugh et al., MER-101-03, A multi center, phase II study to compare MER-101 20mg tablets to intravenous Zometa 4mg in prostate cancer patients. Poster Presentation, May 2009.
Nagae et al., Acidic microenvironment created by osteoclasts causes bone pain associated with tumor colonization. J. Bone Miner. Metab. (2007) 25: 99-104.
Nagae et al., Osteoclasts play a part in pain due to the inflammation adjacent to bone. Bone 39 (2006) 1107-1115.
Nagakura et al., Allodynia and hyperalgesia in adjuvant-induced arthritic rats: time course of progression and efficacy of analgesics. The Journal of Pharmacology and Experimental Therapeutics 306: 490-497, 2003.
Orazol(R): Novel approach to adjuvant therapy for improving outcomes in breast cancer. Merrion Pharmaceuticals, accessed 2013.
Reid et al., Intravenous Zoledronic Acid in Postmenopausal Women with Low Bone Mineral Density. N. Engl. J. Med., vol. 346, No. 9, 2002.
Ringe et al., A review of bone pain relief with ibandronate and other bisphosphonates in disorders of increased bone turnover. Clin. Exp. Rheumatol. 2007; 25: 766-774.
Study: The Use of Zoledronic Acid to Complex Regional Pain Syndrome (Aclasta) sponsored by University of Sao Paulo General Hospital. 2012. Clinical Trials.gov. Accessed on Apr. 5, 2013 at http://clinicaltrials.gov/ct2/show/NCT01788176.
US Product Label for Zometa, accessed 2013.
Walker et al., Disease modifying and anti-nociceptive effects of the bisphosphonate, zoledronic acid in a model of bone cancer pain. Pain 100 (2002) 219-229.
Zaspel et al., Treatment of early stage CRPS I—cortisone (methylprednisolone) versus bisphosphonate (zoledronic acid). German Congress of Orthopedics and Traumatology. 71st Annual Meeting of the German Society of Trauma Surgery, 93rd Meeting of the German Society for Orthopedics and Orthopedic Surgery, 48th Meeting of the Professional Association of Specialists in Orthopedics. Berlin, Oct. 24-27, 2007. German Medical Science GMS Publishing House; 2007.
Zoledronate Disodium: Treatment of Tumor-Induced Hypercalcemia Angiogenesis Inhibitor, Drugs of the Future 2000, 25(3) 259-268.
Zometa FDA Pharmacology Review, part 1, accessed 2013.
Zometa FDA Pharmacology Review, part 2, accessed 2013.
Zometa FDA Pharmacology Review, part 3, accessed 2013.
Zometa FDA Pharmacology Review, part 4, accessed 2013.
Zometa FDA Pharmacology Review, part 5, accessed 2013.

(56) References Cited

OTHER PUBLICATIONS

Sebastin, Complex rgional pain syndrome, Indian J. Past Surg., 4492): 298-307 (2011).

Kim et al, Analgesic effects of the non-nitrogen-containing bisphosphonates etidronate and clodronate, independent of anti-resorptive effects on bone, European Journal of Pharmacology, vol. 699, Issues 1-3, 15, Jan. 15, 2013, pp. 14-22 (Available online: Nov. 28, 2012).

Weiss et al., Biodistribution and Plasma Protein Binding of Zoledronic Acid, Drug Metabolism and Disposition, vol. 36, No. 10, pp. 2043-2049, 2008.

* cited by examiner

COMPOSITIONS COMPRISING RANK/RANKL ANTAGONISTS AND RELATED COMPOUNDS FOR TREATING PAIN

BACKGROUND

The receptor activator of nuclear factor κB (RANK), receptor activator of nuclear factor κB ligand (RANKL), and osteoprotegerin (OPG) triad (RANK/RANKL/OPG) play an important role in immune response and bone metabolism. RANK/RANKL triggers a network of TRAF-mediated kinase cascades that promote osteoclast differentiation. RANKL is expressed on osteoblast cells and its receptor, RANK, on pre-osteoclastic cells. The RANK/RANKL interaction induces the differentiation and formation of multi-nucleated mature osteoclasts, causing bone resorption. The third protagonist, OPG, is also produced by osteoblasts and exerts an inhibitory effect on the pre-osteoclastic differentiation process. OPG, by binding to RANKL, inhibits the RANK/RANKL interaction and subsequent osteoclastogenesis.

SUMMARY

Described herein are dosage forms comprising RANK/RANKL antagonists for treatment of various diseases or medical conditions.

Some embodiments include a method for treating pain comprising administering a polypeptide, a protein, or a nucleic acid to a mammal in need thereof, wherein the polypeptide, the protein, or the nucleic acid is a RANK/RANKL antagonist.

Some embodiments include use of a polypeptide, a protein, or a nucleic acid for treating a disease or medical condition, such as pain, in a mammal in need thereof, wherein the polypeptide, the protein, or the nucleic acid is a RANK/RANKL antagonist.

Some embodiments include use of a polypeptide, a protein, or a nucleic acid in the manufacture of a medicament for treating a disease or medical condition, such as pain, in a mammal, wherein the polypeptide, the protein, or the nucleic acid is a RANK/RANKL antagonist.

DETAILED DESCRIPTION

Figure 1:
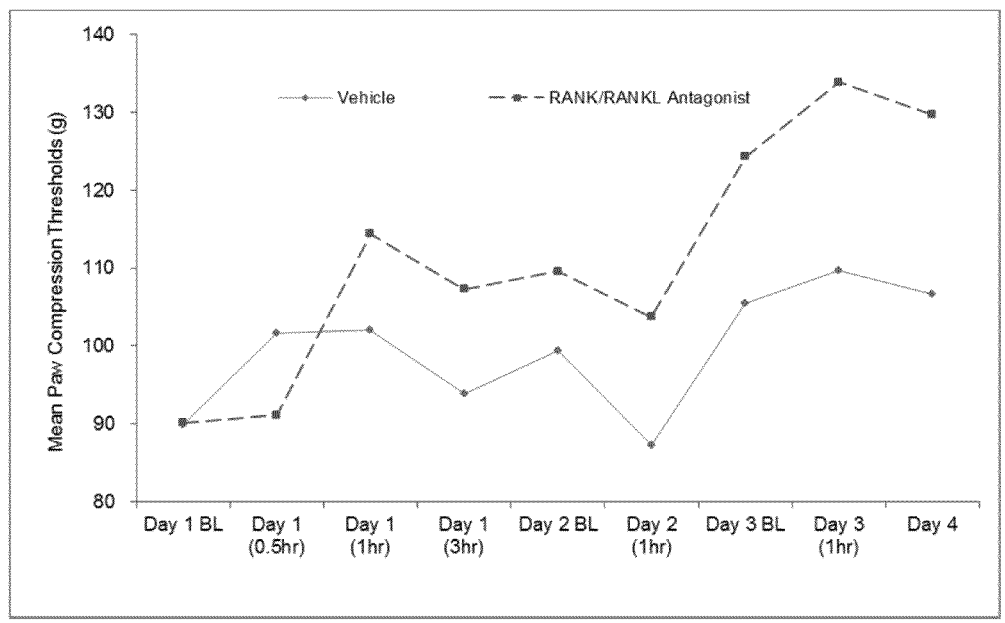
FIG. 1 is a graph depicting the mean paw compression thresholds of rats treated with vehicle or RANK/RANKL antagonism over time in a rat model of inflammatory pain.

Provided herein are methods and compositions for treating undesirable conditions or diseases, including pain. Generally, the patient is a human, but the methods described herein may be applied to any mammal, including domestic animals such as pets and farm animals. Typically, a patient in need of treatment receives an amount of a RANK/RANKL antagonist that is effective to treat pain or another undesirable condition.

Some embodiments relate to the treatment of pain or other undesirable conditions by blocking RANK/RANKL function. For example, an effective amount of one or more RANK/RANKL antagonists can be administered to a mammal, such as a human being, for the treatment of pain or another undesirable condition.

A RANK/RANKL antagonist can be any chemical species having the activity of RANK/RANKL antagonists as commonly understood in the art, or can be an agent that partially or fully blocks, inhibits, or neutralizes one or more biological activities of RANKL or RANK, such as binding of RANKL to RANK, in vitro, in situ, or in vivo. An antagonist may function in a direct or indirect manner. For instance, the antagonist may directly bind to RANKL or RANK, thus partially or fully blocking, inhibiting or neutralizing one or more biological activities of RANKL or RANK, in vitro, in situ, or in vivo. The antagonist may also function indirectly to partially or fully block, inhibit or neutralize one or more biological activities of RANKL or RANK, in vitro, in situ, or in vivo as a result of interacting with, e.g., activating, inducing, blocking or inhibiting, another compound that can bind to RANK or RANKL. The antagonist may also function indirectly to partially or fully block, inhibit or neutralize one or more biological activities of RANKL or RANK, in vitro, in situ, or in vivo as a result of modulating or affecting the production of RANKL or RANK.

"Treatment," "treating," or "therapy" includes its common meaning in the field and includes diagnosis, cure, mitigation, treatment, and prevention.

A RANK/RANKL antagonist can comprise a biomolecule, such as a polypeptide or a protein, a nucleic acid, a polysaccharide, etc., or could be a small molecule, such as a compound having a molecular weight that is less than about 2000, about 1000, about 500, etc. "Polypeptide" as used herein includes its common meaning in the field as well as molecules derived from two amino acids or more.

A RANK/RANKL antagonist can be administered with one or more additional therapeutically active agents. For example, a RANK/RANKL antagonist can be administered simultaneously or administered consecutively with a second therapeutically active agent.

There are a variety of polypeptides and proteins that can be suitable RANK/RANKL antagonists. In some embodiments, the RANK/RANKL antagonist can be a protein that can be derived from the same species of animal as the patient or subject.

In some embodiments, patients in need thereof can treated by administering a RANK/RANKL antagonist comprising a soluble RANK protein that is capable of binding RANKL that can comprise all or a fragment of the extracellular domain of a RANK protein. The patient can be a human and the soluble RANK can be derived from a human RANK polypeptide. RANK/RANKL antagonists comprising a soluble RANK polypeptide may include other portions of RANK besides the extracellular domain but do not include the transmembrane region.

In some embodiments, fusion proteins comprising a soluble RANK for use as antagonists suitable for the methods described herein are those described in US 2003/0021785 A1, which is incorporated here in full by reference.

In some embodiments, soluble RANK polypeptides suitable for the methods described herein can be those described in US 2003/0021785 A1, which is incorporated here in full by reference.

In some embodiments, soluble RANK proteins for use as antagonists suitable for the methods described herein are those described in US 2003/0021785 A1, which is incorporated here in full by reference.

The terms "OPG" or "osteoprotegerin" or "OPG receptor" include their common meaning in the field and includes "native sequence OPG polypeptides" and "OPG variants" (which are further defined herein). "OPG" can be a designation given to those polypeptides which can be encoded by the nucleic acid molecules comprising the polynucleotide sequences shown in Simonet et al., Cell, 89:309 (1997) and variants thereof, as well as fragments of any of the sequences referred to above. The OPG polypeptides may be isolated from a variety of sources, such as from human tissue or cells or from another source, or prepared by recombinant and/or synthetic methods. A "native sequence" OPG polypeptide includes its common meaning in the field and additionally includes the following: comprises a polypeptide having the same amino acid sequence as the corresponding OPG polypeptide derived from nature. Such native sequence OPG polypeptides can be isolated from nature or can be produced by recombinant and/or synthetic means. The term "native sequence OPG polypeptide" includes its common meaning in the field and additionally includes the following: specifically encompasses naturally-occurring truncated or secreted forms (e.g., an extracellular domain sequence), naturally-occurring variant forms (e.g., alternatively spliced forms) and naturally-occurring allelic variants of the polypeptide. The OPG polypeptides include the polypeptides described as "FDCR-1" and "OCIF" in Yasuda et al., Endocrinology, 139:1329 (1998) and Yun et al., J. Immunol., 1 61:61 13-6121 (1998).

"OPG variant" includes its common meaning in the field and includes an OPG polypeptide having at least about 80% amino acid sequence identity with the amino acid sequence of a native sequence OPG or OPG ECD. In some embodiments, the OPG variant binds to RANKL, such as, to the full length RANK Ligand.

An "extracellular domain" or "ECD" include their common meaning in the field and include: a form of the polypeptide which is essentially free of the transmembrane and cytoplasmic domains. Ordinarily, an ECD form of a polypeptide will have less than about 1% of such transmembrane and/or cytoplasmic domains and possibly, will have less than about 0.5% of such domains. It can be understood that any transmembrane domain(s) identified for the polypeptides can be identified pursuant to criteria routinely employed in the art for identifying that type of hydrophobic domain. The exact boundaries of a transmembrane domain may vary. In some embodiments, the boundaries of a transmembrane domain varies by no more than about 5 amino acids at either end of the domain as initially identified. In some embodiments, the ECD will consist of a soluble, extracellular domain sequence of the polypeptide which is free of the transmembrane and cytoplasmic or intracellular domains (and is not membrane bound).

A "liposome" includes its common meaning in the field and includes: a small vesicle composed of various types of lipids, phospholipids and/or surfactant which can be useful for delivery of a drug (such as a polypeptide or antibody thereto) to a mammal. The components of the liposome can be commonly arranged in a bilayer formation, similar to the lipid arrangement of biological membranes.

The term "antibody" includes its common meaning in the field and includes use in the broadest sense, and additionally, specifically covers, for example, single monoclonal antibodies which can bind RANKL or RANK, antibody compositions with polyepitopic specificity, single chain antibodies, and fragments of antibodies.

Some RANK/RANKL antagonists may comprise an antibody, such as a monoclonal antibody.

The term "monoclonal antibody" as used herein includes its common meaning in the field and includes: an antibody obtained from a population of substantially homogeneous antibodies, i.e., the individual antibodies comprising the population can be identical except for possible naturally occurring mutations that may be present in minor amounts. Monoclonal antibodies can be highly specific, being directed against a single antigenic site. Furthermore, in contrast to conventional (polyclonal) antibody preparations which typically include different antibodies directed against different determinants (epitopes), each monoclonal antibody can be directed against a single determinant on the antigen. In addition to their specificity, the monoclonal antibodies can be advantageous in that they can be synthesized by hybridoma culture, uncontaminated by other immunoglobulins. The modifier "monoclonal" includes its common meaning in the field and indicates the character of the antibody as being obtained from a substantially homogeneous population of antibodies, and is not to be construed as requiring production of the antibody by any particular method. For example, the monoclonal antibodies may be made by the hybridoma method first described by Kohler et al., Nature, 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein specifically include "chimeric" antibodies (immunoglobulins) which includes its common meaning in the field and includes: a portion of the heavy and/or light chain can be identical to or homologous with corresponding sequences in antibodies derived from a particular species or belonging to a particular antibody class or subclass, while the remainder of the chain(s) can be identical to or homologous with corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851-6855 (1984)). Methods of making chimeric antibodies are known in the art.

"Humanized" forms of non-human (e.g., murine) antibodies can be chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies can be human immunoglobulins (recipient antibody) in which residues from a complementarity-determining region (CDR) of the recipient can be replaced by residues from a CDR of a non-human species (donor antibody) such as mouse, rat or rabbit having the desired specificity, affinity, and capacity. In some instances, Fv framework region (FR) residues of the human immunoglobulin can be replaced by corresponding non-human residues. Furthermore, humanized antibodies may comprise residues which can be found neither in the recipient antibody nor in the imported CDR or framework sequences. These modifications can be made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions can be those of a human immunoglobulin sequence.

The humanized antibody optimally also will comprise at least a portion of an immunoglobulin constant region (Fc), typically that of a human immunoglobulin. For further details, see Jones et al., Nature, 321:522-525 (1986); Reichmann et al., Nature, 332:323-329 (1988); and Presta, Curr. Op. Struct. Biol., 2:593-596 (1992). The humanized antibody may be an antibody wherein the antigen-binding region of the antibody can be derived from an antibody produced by immunizing macaque monkeys with the antigen of interest. Methods of making humanized antibodies are known in the art.

Human antibodies can also be produced using various techniques known in the art, including phage-display libraries. Hoogenboom and Winter, J. Mol. Biol., 227:381 (1991); Marks et al., J. Mol. Biol., 222:581 (1991). The techniques of Cole et al. and Boerner et al. are also available for the preparation of human monoclonal antibodies. Cole et al., Monoclonal Antibodies and Cancer Therapy, Alan R. Liss, p. 77 (1985); Boerner et al., J. Immunol., 147(1):86-95 (1991).

"Antibody fragments" comprise a portion of an intact antibody, such as the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen-combining sites and can be still capable of cross-linking antigen.

"Fv" can be the minimum antibody fragment which contains a complete antigen-recognition and binding site. This region consists of a dimer of one heavy- and one light-chain variable domain in tight, non-covalent association. It can be in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site. The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five known major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the $V_H$ and $V_L$ domains of antibody, wherein these domains are present in a single polypeptide chain. The Fv polypeptide further comprises a polypeptide linker between the $V_H$ and $V_L$ domains which can enable the sFv to form the desired structure for antigen binding. For a review of sFv, see Pluckthun in The Pharmacology of Monoclonal Antibodies, vol. 1 13, Rosenburg and Moore eds., Springer-Verlag, New York, pp. 269-315 (1994).

The term "diabodies" includes its common meaning in the field and includes: small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains can be forced to pair with the complementary domains of another chain and create two antigen-binding sites. Diabodies are described more fully in, for example, EP 404,097; WO 93/011161; and Hollinger et al., Proc. Natl. Acad. Sci. USA, 90:6444-6448 (1993). An antibody that "specifically binds to" or can be "specific for" a particular polypeptide or an epitope on a particular polypeptide can be one that binds to that particular polypeptide or epitope on a particular polypeptide without substantially binding to any other polypeptide or polypeptide epitope.

In some embodiments, the RANKL antagonist can be an OPG (osteoprotegerin) variant or an anti-RANKL antibody; the RANKL antagonist can be a monoclonal anti-RANKL antibody; the RANKL antagonist can be a humanized monoclonal anti-RANKL antibody; the RANKL antagonist can be denosumab; or the RANKL antagonist can be OPG.

In some embodiments, the RANK/RANKL antagonist can be denosumab. Denosumab is a fully human antibody that shares the pharmacological attributes of OPG, in that both bind to and inhibit RANKL. Additionally, denosumab can have a significant longer half-life than OPG, allowing less frequent administration. In some embodiments, the RANK/RANKL antagonist can be OPG. Further description of denosumab may be found in WO 2013/181575 A2, which is incorporated here in full by reference.

In some embodiments, the RANK/RANKL antagonist can be an OPG (osteoprotegerin) variant or an anti-RANKL antibody. In some embodiments, the RANK/RANKL antagonist can be a monoclonal anti-RANKL antibody. In some embodiments, the RANK/RANKL antagonist can be a small interfering RNA, a microRNA, a precursor molecule, a ribozyme, an antisense nucleic acid sequence, or an aptamer targeting RANKL. In some embodiments, the RANK/RANKL antagonist can be a humanized monoclonal anti-RANKL antibody.

In some embodiments, the nucleic acid molecules encoding a soluble RANK for use as a RANK/RANKL antagonist suitable for the methods described herein are those described in US 2003/0021785 A1, which is incorporated here in full by reference.

In some embodiments, antisense RNA and DNA molecules for use as antagonists suitable for the methods described herein are those described in US 2003/0021785 A1, which is incorporated here in full by reference.

Small interfering RNA (short interfering RNA, silencing RNA, siRNA) can be a class of double-stranded RNA-molecules, which can be 19-30 nucleotides, such as 20-25 nucleotides long. siRNAs inhibit expression of a specific gene via RNA-interference. siRNAs can be cut from long double-stranded RNAs by the RNase III Dicer. They can also be derived by chemical synthesis. They also play a role in antiviral mechanisms or in shaping the chromatin structure of a genome. In molecular research, synthetic siRNAs can also be used in RNA-interference (RNAi) to downregulate the expression of specific target genes. With their ability to knock down essentially any gene of interest, siRNAs can been used to knock down RANK or RANKL. MicroRNAs (miRNAs) can be posttranscriptional regulators that bind to complementary sequences in the 3'UTR of mRNA transcripts, usually resulting in gene silencing. They can be short RNA molecules which can be about 22 nucleotides long.

Precursor molecules, e.g. precursor molecules of siRNA and/or miRNA, may be substrates for the siRNA/miRNA-biogenesis-apparatus of the target cell. This comprises, for example, RNA precursor molecules such as double-stranded RNA (dsRNA) or short hairpin RNA-molecules (shRNA), which can be processed by endonucleases such as Drosha and/or Pasha to siRNA molecules or miRNA molecules, respectively. In some embodiments, dsRNA-molecules or short hairpin RNA-molecules (shRNA) having a length of more than 27 nucleotides, more than 30 up to 100 nucleotides or longer, or dsRNA molecules having a length of 30-50 nucleotides, can be used.

Further precursor molecules may be DNA constructs encoding dsRNA, shRNA, siRNA and/or miRNA, whereby the coding elements can be controlled by regulatory elements allowing an expression of dsRNA, shRNA, siRNA, and/or miRNA in the target cell. Examples for such control elements can be polymerase II or promoters or polymerase III promoters such as, for example, U6 or H1. Ribozymes can be catalytic RNAs which possess a well defined structure that enables them to catalyze a chemical reaction. Apart from naturally occurring ribozymes they can be made artificially and be tailored to interact with nucleic acids and proteins.

Antisense oligonucleotides can be single strands of DNA or RNA that can be complementary to a chosen sequence. They can be between 10 and 35 nucleotides long, such as about 20-25 nucleotides. Antisense DNA oligonucleotides can target specific, complementary RNA, and upon binding DNA/RNA hybrids can be formed. Antisense RNA oligonucleotides can bind to mRNA by binding to mRNA strands.

Aptamers can be oligonucleic acid (DNA or RNA aptamers) or peptide molecules (peptide aptamers) that bind to a specific target molecule. Aptamers can be used for therapeutic purposes as macromolecular drugs. Aptamers can be created by selecting them from a large random sequence pool.

A RANK/RANKL antagonist can be a small molecule, e.g. a compound that is not a biomolecule, such as a compound having a molecular weight below about 2000, Daltons, 1000 Daltons, or 500 Daltons.

Some Bruton's tyrosine kinase (BTK) inhibitors can be RANK/RANKL antagonists. BTK is primarily expressed in B cells, myeloid and erythroid progenitor cells.

BTK inhibitors can include ONO-4059; ibrutinib; Benzo[b]thiophene-2-carboxamide, N-[3-[6-[[4-[(2R)-1,4-dimethyl-3-oxo-2-piperazinyl]phenyl]amino]-4,5-dihydro-4-methyl-5-oxo-2-pyrazinyl]-2-methylphenyl]-4,5,6,7-tetrahydro-(GDC-0834); RN-486; Benzamide, 4-(1,1-dimethylethyl)-N-[3-[8-(phenylamino)imidazo[1,2-a]pyrazin-6-yl]phenyl]-(CGI-560); Benzamide, N-[3-[4,5-dihydro-4-methyl-6-[[4-(4-morpholinylcarbonyl)phenyl]amino]-5-oxo-2-pyrazinyl]-2-methylphenyl]-4-(1,1-dimethylethyl)-(CGI-1746CAS Registry No. 910232-84-7); HM-71224; 2-Propenamide, N-[3-[[5-fluoro-2-[[4-(2-methoxyethoxy)phenyl]amino]-4-pyrimidinyl]amino]phenyl]-(CC-292, CAS Registry No. 1202757-89-8); 2-Pyridinecarboxamide, 4-[4-[[5-fluoro-4-[[3-[(1-oxo-2-propen-1-yl)amino]phenyl]amino]-2-pyrimidinyl]amino]phenoxy]-N-methyl-(CNX-774, CAS Registry No. 1202759-32-7), AVL-101 (CAS Registry No. 1552307-34-2), AVL-291 (CAS Registry No. 1552307-35-3), and AVL-292 (CAS Registry No. 1552307-36-4), [N-(2-chloro-6-methylphenyl)-2-(6-(4-(2-hydroxyethyl) piperazin-1-yl)-2-methylpyrimidin-4-ylamino)thiazole-5-carboxamide] (dasatinib), alpha-cyano-beta-hydroxy-beta-methyl-N-(2,5-ibromophenyl) propenamide (LFM-A13), and ONO-WG-307.

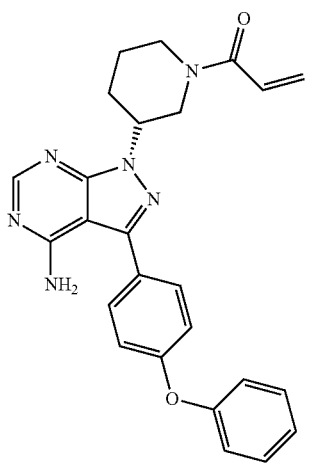

Ibrutinib

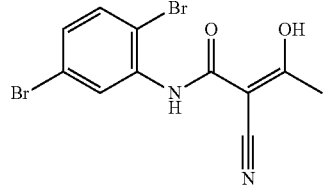

LFM-A13

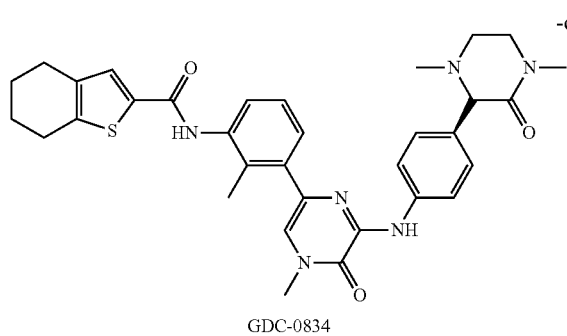

GDC-0834

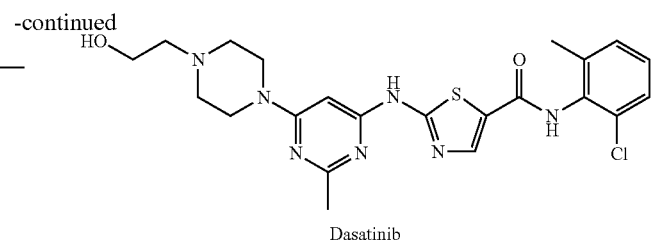

Dasatinib

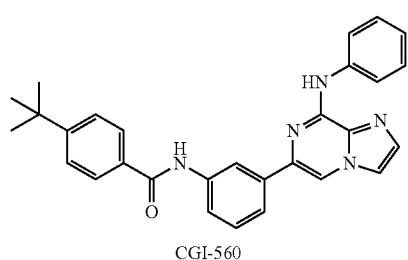

CGI-560

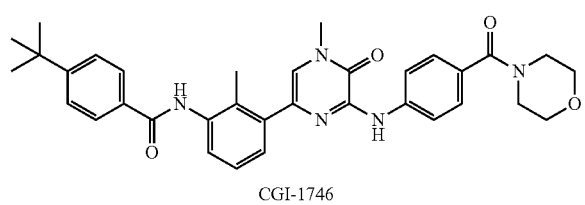

CGI-1746

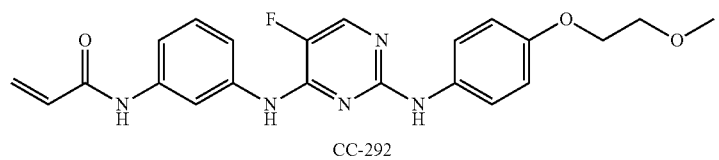

CC-292

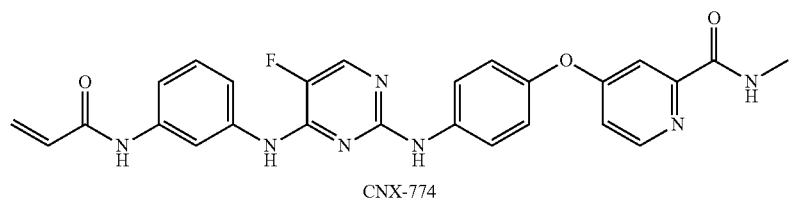

CNX-774

ONO-4059 has been shown to dose-dependently inhibit RANKL-driven osteoclast differentiation by 70% ($IC_{50}$: 0.853 nmol/L) (Ariza, *Yuko*, Yoshizawa, Toshio, Ueda, Yoshiko, Hotta, Shingo, Narita, Masami, Kawabata, Kazuhito; ONO-4059—A Novel Small Molecule Bruton's Tyrosine Kinase (Btk) Inhibitor, Suppresses Osteoclast Differentiation and Activation. [abstract]. Arthritis Rheum 2012; 64 Suppl 10:1799)

Compounds such as pamidronate or pamidronic acid, incadronate or incadronic acid, ibandronate or ibandronic acid, risedronate or risedronic acid, zoledronate or zoledronic acid, minodronate or minodronic acid, cimadronate or cimadronic acid, etc., may be RANK/RANKL antagonists.

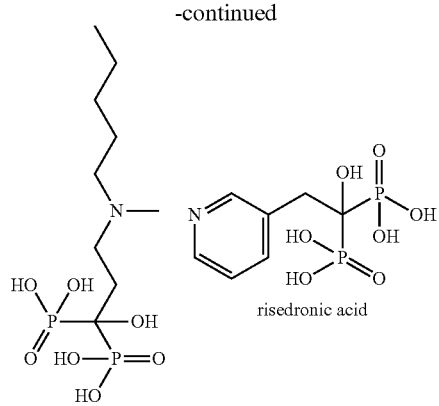

ibandronic acid risedronic acid

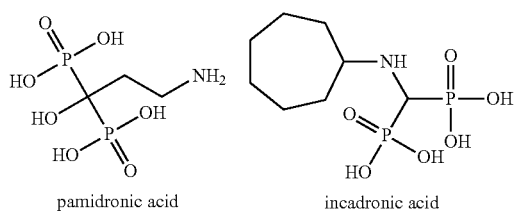

pamidronic acid    incadronic acid

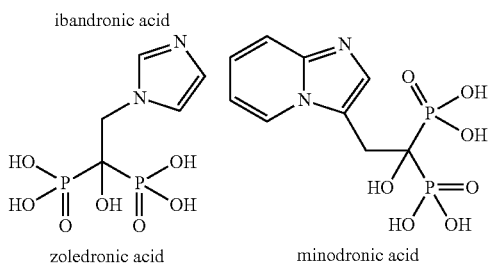

zoledronic acid    minodronic acid

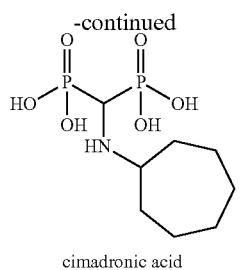

cimadronic acid

Zoledronic acid has been shown to "markedly increase[ ] OPG protein secretion and reduce[ ] transmembrane RANKL protein expression" (Pan et al. 2004, J. Bone Miner. Res. 2004 January; 19(1): 147-154).

Minodronic acid has been shown to "inhibit[ ] RANKL expression in a cultured bone marrow stromal cell line." (Nishida, et al., Biochemical and Biophysical Research Communications 328 (2005) 91-97).

In some embodiments, the RANK/RANKL antagonist is zoledronic acid.

In some embodiments, the RANK/RANKL antagonist is minodronic acid.

In some embodiments, the RANKL antagonist is zoledronic acid.

In some embodiments, the RANKL antagonist is minodronic acid.

Some RANK/RANKL antagonists are RANKL antagonists as understood in the art, or include any molecule that partially or fully blocks, inhibits, or neutralizes a biological activity of RANKL. This includes, but is not limited to, soluble forms of OPG or RANK, such as an extracellular domain sequence of RANK, OPG immunoadhesins, RANK immunoadhesins, OPG fusion proteins, RANK fusion proteins, covalently modified forms of OPG, covalently modified forms of RANK, OPG variants, RANK variants, OPG antibodies, RANK antibodies, and RANKL antibodies.

Some RANK/RANKL antagonists are RANK antagonists as understood in the art, or include any molecule that partially or fully blocks, inhibits, or neutralizes a biological activity of RANK.

Unless otherwise indicated, any reference to a RANK/RANKL antagonists by structure, name, or any other means, includes pharmaceutically acceptable salts, such as sodium, potassium, and ammonium salts; prodrugs, such as ester prodrugs; alternate solid forms, such as polymorphs, solvates, hydrates, etc.; tautomers; or any other chemical species that may rapidly convert to a compound described herein under conditions in which the compounds are used as described herein.

If stereochemistry is not indicated, a name or structural depiction includes any stereoisomer or any mixture of stereoisomers.

Generally, an oral dosage form comprising a small molecule RANK/RANKL antagonist such as ibrutinib, zoledronic acid, or minodronic acid, can be administered orally to a mammal, such as a human being, at least once, to treat a disease or condition, or to relieve pain A RANK/RANKL antagonist, such as an antibody (e.g., denosumab), or a small molecule such as ibrutinib, zoledronic acid, or minodronic acid, may be used to treat, or provide relief of, any type of pain including, but not limited to, back pain, pain in an extremity, arthralgia, muscle pain or myalgia, inflammatory pain, arthritis pain, complex regional pain syndrome, lumbosacral pain, musculoskeletal pain, neuropathic pain, chronic pain, cancer-related pain, acute pain, postoperative pain, rheumatoid arthritis, osteoarthritis, erosive osteoarthritis, axial spondyloarthritis including ankylosing spondylitis, acute vertebral crush fracture, fibrous dysplasia, SAPHO syndrome, osteoporosis, transient osteoporosis, or transient osteoporosis of the hip etc. In some embodiments, a RANK/RANKL antagonist, such as an antibody (e.g., denosumab), or a small molecule such as ibrutinib, zoledronic acid, or minodronic acid, may be used to treat, or provide relief of, any type of pain including, but not limited to, inflammatory pain, arthritis pain, complex regional pain syndrome, lumbosacral pain, musculoskeletal pain, neuropathic pain, chronic pain, cancer-related pain, acute pain, postoperative pain, fibromyalgia, etc. In some instances, pain relief may be palliative, or pain relief may be provided independent of improvement of the disease or condition or the underlying cause of the disease or condition. For example, although the underlying disease may not improve, or may continue to progress, an individual suffering from the disease may experience pain relief. In some embodiments, enhanced bioavailability of the zoledronic acid or minodronic acid may be achieved in treating one of these conditions by administering a dosage form comprising zoledronic acid in the form of a disodium salt. This may allow a reduced molar amount of the disodium salt to be used as compared to what would be used with the diacid form.

In some embodiments, the RANK/RANKL antagonist, such as an antibody (e.g., denosumab), or a small molecule such as ibrutinib, zoledronic acid, or minodronic acid, may be administered to relieve inflammatory pain including musculoskeletal pain, arthritis pain, and complex regional pain syndrome.

In some embodiments, a RANK/RANKL antagonist, such as an antibody (e.g., denosumab), or a small molecule such as ibrutinib, zoledronic acid, or minodronic acid, may be administered orally to relieve inflammatory pain including musculoskeletal pain, arthritis pain, and complex regional pain syndrome.

With respect to use of a RANK/RANKL antagonist, such as an antibody (e.g., denosumab), or a small molecule such as ibrutinib, zoledronic acid, or minodronic acid, for relieving pain associated with an inflammatory condition or musculoskeletal pain, relief of pain can be short-term, e.g. for a period of hours after administration of the dosage form, and/or relief of pain can be long-term, e.g. lasting for days, weeks, or even months after administration of the RANK/RANKL antagonist. In some embodiments, a mammal, such as a human being, experiences pain relief at least about 3 hours, at least about 6 hours, at least about 12 hours, at least about 24 hours, at least about 48 hours, at least about one week, at least about 2 weeks, or at least about 3 weeks, at least about 1 month, at least about 2 months, at least about 3 months, at least about 6 months, after administration of denosumab, minodronic acid, or oral zoledronic acid. In some embodiments, a mammal, such as a human being, experiences pain relief during at least part of the time from about 3 hours to about 2 weeks, about 3 hours to about 3 weeks, about 3 hours to about 24 hours, about 6 hours to about 2 weeks, or about 6 hours to about 24 hours, about 3 days to about 2 weeks, about 6 days to about 2 weeks, at least about 1 month, at least about 2 months, at least about 3 months, at least about 6 months, after administration of denosumab, minodronic acid, or oral zoledronic acid.

A RANK/RANKL antagonist, such as an antibody (e.g., denosumab), or a small molecule such as ibrutinib, zoledronic acid, or minodronic acid, may be administered to relieve musculoskeletal pain including back pain (such as low back pain), and pain associated with rheumatoid arthritis, juvenile rheumatoid arthritis, osteoarthritis, erosive osteoarthritis, sero-negative (non-rheumatoid) arthropathies, non-articular rheumatism, peri-articular disorders, axial spondyloarthritis including ankylosing spondylitis, Paget's disease of bone, fibrous dysplasia, SAPHO syndrome, transient osteoarthritis of the hip, vertebral crush fractures, osteoporosis, etc.

Examples of musculoskeletal pain include back pain (such as low back pain); and pain associated with vertebral crush fractures, fibrous dysplasia, osteogenesis imperfecta, Paget's disease of bone, transient osteoporosis, and transient osteoporosis of the hip.

A RANK/RANKL antagonist, such as an antibody (e.g., denosumab), or a small molecule such as ibrutinib, zoledronic acid, or minodronic acid, may also be used to treat bone fractures or to enhance the healing of bone fractures.

A RANK/RANKL antagonist, such as an antibody (e.g., denosumab), or a small molecule such as ibrutinib, zoledronic acid, or minodronic acid, may also be used to treat low back pain, or other musculoskeletal or inflammatory conditions, having a change in bone that is detectable by MRI or another medical imaging instrument. For example, a RANK/RANKL antagonist may be used to treat low back pain associated Modic changes, or vertebral endplate signal changes (VESC) and bone marrow changes visible using magnetic resonance imaging (MRI). Modic changes, can be classified into various types including type 1 (M1), type 2 (M2), and type 3 (M3) lesions or changes, any of which may be treated using a RANK/RANKL antagonist. VESCs may be found in patients with different types of low back pain including but not limited to spondylitis, trauma, spondyloarthropathies including ankylosing spondylitis, Schmorl's nodes, fracture, tumor, and spinal cord infarction. Lesions in ankylosing spondylitis include osteitis and spondylodiscitis which can be detected using MRI or another medical imaging instrument. Treatment with a RANK/RANKL antagonist, such as an antibody (e.g. denosumab) or an oral or intravenous small molecule (such as ibrutinib, zoledronic acid, or minodronic acid) may reduce the size of, or prevent the growth or progression of changes in bone that are detectable on MRI (e.g. Modic changes, VESC, bone marrow changes, bone marrow edema, etc.).

A RANK/RANKL antagonist, such as an antibody (e.g., denosumab), or a small molecule such as ibrutinib, zoledronic acid, or minodronic acid, may also be used to treat arthritis. Arthritis refers to inflammatory joint diseases that can be associated with pain. Examples of arthritis pain include pain associated with osteoarthritis, erosive osteoarthritis, rheumatoid arthritis, juvenile rheumatoid arthritis, psoriatic arthritis, sero-negative (non-rheumatoid) arthropathies, non-articular rheumatism, peri-articular disorders, neuropathic arthropaties including Charcot's foot, axial spondyloarthritis including ankylosing spondylitis, and SAPHO syndrome.

A RANK/RANKL antagonist, such as an antibody (e.g., denosumab), or a small molecule such as ibrutinib, zoledronic acid, or minodronic acid, may also be used to treat arthritis, such as osteoarthritis of the knee, including arthritis or osteoarthritis of the knee associated with bone marrow lesions (BML), including BML that may be detected using MRI or another medical imaging instrument. In some embodiments, a RANK/RANKL antagonist may be used to treat arthritis or osteoarthritis of the knee associated with bone marrow edema (BME), including BME which may be detected using MRI or another medical imaging instrument.

In some embodiments, a human being that is treated for a disease or condition, such as an inflammatory condition, e.g. arthritis, with a RANK/RANKL antagonist, has an age of about 10 years to about 90 years, about 20 years to about 80 years, about 30 years to about 75 years old, about 40 years to about 70 years, about 1 year to about 16 years, or about 80 years to about 95 years.

In some embodiments, a human being that is treated for a disease or condition, such as an inflammatory condition or musculoskeletal pain, e.g. arthritis, with a RANK/RANKL antagonist, has suffered from the disease or condition for at least 1 month, at least 2 months, at least 6 months, or at least 1 year.

In some embodiments, the disease or condition, such as an inflammatory condition, e.g. arthritis, affects a knee, an elbow, a finger, a toe, a wrist, a shoulder, or a hip.

In some embodiments, the RANK/RANKL antagonist, such as an antibody (e.g., denosumab), or a small molecule such as ibrutinib, zoledronic acid, or minodronic acid, may also be administered to relieve neuropathic pain, including diabetic peripheral neuropathy, post-herpetic neuralgia, trigeminal neuralgia, monoradiculopathies, phantom limb pain, and central pain. Other causes of neuropathic pain include cancer-related pain, lumbar nerve root compression, spinal cord injury, post-stroke pain, central multiple sclerosis pain, HIV-associated neuropathy, and radio-therapy or chemo-therapy associated neuropathy. In some embodiments, enhanced bioavailability of the zoledronic acid may be achieved in treating one of these conditions by administering a dosage form comprising zoledronic acid in the form of a disodium salt. This may allow a reduced molar amount of the disodium salt to be used as compared to what would be used with the diacid form.

In some embodiments, administration of a RANK/RANKL antagonist, such as an antibody (e.g., denosumab), or a small molecule such as ibrutinib, zoledronic acid, or minodronic acid, may also be useful to treat hypercalcemia of malignancy, multiple myeloma, bone metastases from solid tumors, Paget's disease of bone, giant cell tumor of bone, blood cancers or leukemias, or solid tumors or cancers.

In some embodiments, the mammal being treated may not be suffering from bone metastasis. In some embodiments, the mammal being treated may not be suffering from cancer. In some embodiments, the mammal being treated may not be suffering from osteoporosis. In some embodiments, if the mammal has osteoporosis or cancer, the mammal is being treated for pain that is not a result of osteoporosis or cancer. In some embodiments, if the mammal has osteoporosis or cancer, a second therapeutic agent is administered to the mammal for the treatment of osteoporosis or cancer, and wherein the second therapeutic agent is not a RANK/RANKL antagonist.

A RANK/RANKL antagonist, such as an antibody (e.g., denosumab), or a small molecule such as ibrutinib, zoledronic acid, or minodronic acid, may also be administered to relieve cancer-related pain, including pain associated with multiple myeloma and bone metastases from solid tumors. In some embodiments, a RANK/RANKL antagonist is used to treat pain that may not be cancer-related pain. For example, a RANK/RANKL antagonist may be used to treat pain that may not be associated with multiple myeloma, bone metastasis from solid tumors, hypercalcemia of malignancy, giant cell tumor of bone, blood cancers or leukemias, or solid tumors or cancers. In some embodiments, enhanced bioavailability of zoledronic acid or minodronic acid may be achieved in treating one of these conditions by administering a dosage form comprising zoledronic acid or minodronic acid in the form of a disodium salt. This may allow a reduced molar amount of the disodium salt to be used as compared to what would be used with the diacid form.

In some embodiments, a RANK/RANKL antagonist, such as an antibody (e.g., denosumab), or a small molecule such as ibrutinib, zoledronic acid, or minodronic acid, may be administered to relieve complex regional pain syndrome, such as complex regional pain syndrome type I (CRPS-I), complex regional pain syndrome type II (CRPS-II), CRPS-NOS, or another type of CRPS. CRPS is a type of inflammatory pain. CRPS can also have a neuropathic component.

Complex regional pain syndrome is a debilitating pain syndrome. It is characterized by severe pain in a limb accompanied by edema, and autonomic, motor and sensory changes.

In some embodiments, a RANK/RANKL antagonist, such as an antibody (e.g., denosumab), or a small molecule such as ibrutinib, zoledronic acid, or minodronic acid, may be administered to treat fibromyalgia. Fibromyalgia is a condition which may affect the muscles and soft tissue, and may include symptoms in the head, back, neck, shoulder, and/or hip.

In some embodiments, a RANK/RANKL antagonist, such as an antibody (e.g., denosumab), or a small molecule such as ibrutinib, zoledronic acid, or minodronic acid, may also be useful to treat complex regional pain syndrome, rheumatoid arthritis, osteoarthritis, erosive osteoarthritis, axial spondyloarthritis including ankylosing spondylitis, acute vertebral crush fracture, fibrous dysplasia, SAPHO syndrome, osteoporosis, transient osteoporosis, or transient osteoporosis of the hip. In some embodiments, enhanced bioavailability of zoledronic acid or minodronic acid may be achieved in treating one of these conditions by administering a dosage form comprising zoledronic acid or minodronic acid in the form of a disodium salt. This may allow a reduced molar amount of the disodium salt to be used as compared to what would be used with the diacid form.

In some embodiments, administration a RANK/RANKL antagonist, such as an antibody (e.g., denosumab) or an oral small molecule (such as ibrutinib, zoledronic acid, or minodronic acid) may also be useful to treat hypercalcemia of malignancy, multiple myeloma, bone metastases from solid tumors, Paget's disease of bone, giant cell tumor of bone, blood cancers or leukemias, or solid tumors or cancers. In some embodiments, enhanced bioavailability of zoledronic acid or minodronic acid may be achieved in treating one of these conditions by administering a dosage form comprising zoledronic acid or minodronic acid in the form of a disodium salt. This may allow a reduced molar amount of the disodium salt to be used as compared to what would be used with the diacid form.

With respect to the treatment of any condition recited herein, in some embodiments a first dose of the RANK/RANKL antagonist is administered and a second dose of the RANK/RANKL antagonist is administered. The timing of the administration of the two doses may be such that, with respect to the first dose, the second dose with respect to the first dose, the second dose is administered at $5 \times T_{max}$ or greater (e.g., if $T_{max}$ is 1 hour, at 5 hours or later), at least $10 \times T_{max}$ or greater, at least about $15 \times T_{max}$ or greater, at least about $20 \times T_{max}$ or greater, at least about $50 \times T_{max}$ or greater, or at least about $200 \times T_{max}$ or greater, wherein $T_{max}$ is the time of maximum plasma concentration for the first dose.

Some embodiments include treatment of a condition recited herein, such as musculoskeletal pain, inflammatory pain, arthritis, or complex regional pain syndrome, wherein the treatment comprises either: administering only one dose or dosage form to a mammal to treat the condition, or administering a first dose or dosage form to the mammal (e.g. orally), followed by administering a second dose or dosage form to the mammal (e.g. orally). If two or more doses or dosage forms are administered, the second dose or dosage form is administered before the maximum pain relieving effect of the first dose or dosage form is achieved, or before a peak in the pain relieving effect of the first dose or dosage form is experienced by a mammal, receiving the dose or dosage form. In some embodiments, the second dose or dosage form is administered before an observable pain relieving effect is achieved. In some embodiments, the second dose or dosage form is administered about 12 hours to about 60 days, about 24 hours to about 28 days, about 24 hours to about 7 days, about 24 hours to about 14 days, or about 24 hours to about 21 days, after the first dose or dosage form is administered.

Some embodiments include treatment of a condition recited herein, such as musculoskeletal pain, inflammatory pain, arthritis, or complex regional pain syndrome, wherein the treatment comprises administering a first dose or dosage form, such as a first oral dosage form, to the mammal, followed by administering a second dose or dosage form, such as a second oral dosage form, to the mammal, wherein the second dose or dosage form is administered after the maximum pain relieving effect of the first dose or dosage form is achieved, and the second dose or dosage form is administered while the mammal is still experiencing pain relief from the first dose or dosage form, or while the pain relieving effect from the first dose or dosage form is observable. In some embodiments, the second dose or dosage form is administered about 12 hours to about 60 days, about 24 hours to about 28 days, about 24 hours to about 7 days, about 24 hours to about 14 days, or about 24 hours to about 21 days, after the first dose or dosage form is administered.

In addition to relieving pain, administration of a RANK/RANKL antagonist, such as an antibody (e.g., denosumab), or a small molecule such as ibrutinib, zoledronic acid, or minodronic acid, may also be useful to treat diseases or conditions that may or may not include a pain component. For example, a RANK/RANKL antagonist may be useful to treat any of the pain conditions or types of conditions listed above, including treatment that does not simply relieve the pain of those conditions, and treatment that is carried out in such a way that the condition is treated without pain relief occurring. In addition to any pain relief a RANK/RANKL antagonist may or may not provide, a RANK/RANKL antagonist may be used to treat a disease or condition such as a metabolic disease or condition; an inflammatory disease or condition, including an inflammatory disease or condition that might not be associated with pain; a cancer disease or condition; a neurological disease or condition; etc.

The duration of treatment will vary depending upon the particular RANK/RANKL antagonist, the disease or condition being treated, and other factors. For biological molecules such as denosumab repeated doses may be administered over at least a period of two weeks or longer, or may be administered indefinitely. Several rounds of treatment may be given, alternating with periods of no treatment. If discontinued, treatment may be resumed if a relapse of the pain should occur.

For therapeutic use, a RANK/RANKL antagonist can be administered to a mammal, including a human patient, for treatment in a manner appropriate to the indication. Systemic administration may be used. The RANK/RANKL antagonist may be applied locally. For biological molecules such as denosumab, means of local administration include, for example, local injection, or application of the antagonist admixed or polymerized with a slow-release matrix suitable for this purpose, many of which can be known.

In some embodiments, RANK/RANKL antagonists can be concurrently administered with other drugs or therapeutic agents in the manufacture of a medicament for the treatment of pain. RANK/RANKL antagonists and other drugs may be formulated into therapeutic compositions comprising an effective amount of the antagonist.

In some embodiments, therapeutic agents that may be administered in conjunction with the RANK/RANKL antagonists described herein may include therapeutic agents indicated for the treatment of pain or another neurological disorder. In some embodiments, therapeutic agents indicated for the treatment of pain and/or inflammation may include analgesic and/or anti-inflammatory agents, including aspirin (acetylsalicylic acid), nonsteroidal anti-inflammatory drugs (NSAIDs) (e.g., ibuprofen, naproxen, ketoprofen, celecoxib, firocoxib, meloxicam, etc.), acetaminophen, narcotic or opioid pain relievers (e.g., morphine, codeine, fentanyl, oxycodone, hydrocodone, hydromorphone, etc.), and steroids (e.g., triamcinolone, predisone, methylprednisolone, cortisone, etc.).

In some embodiments, sustained-release forms of RANK/RANKL antagonists can be used. Sustained-release forms suitable for use in the disclosed methods include, but are not limited to, soluble RANK polypeptides, and antagonistic anti-RANK or anti-RANKL antibodies that can be encapsulated in a slowly-dissolving biocompatible polymer (such as the alginate microparticles described in U.S. Pat. No. 6,036,978), admixed with a slow-release polymer (including topically applied hydrogels), and/or incorporated into a biocompatible semi-permeable implant.

The amount of RANK/RANKL antagonist administered per dose will vary depending on the antagonist being used and the mode of administration. If the antagonist is a soluble RANK and is administered by injection, the effective amount per adult dose will range from about 0.5 mg/m$^2$ to about 20 mg/m$^2$, about 1 mg/m$^2$ to about 5 mg/m$^2$, about 3 mg/m$^2$ to about 10 mg/m$^2$, about 5 mg/m$^2$ to about 10 mg/m$^2$, about 7 mg/m$^2$ to about 12 mg/m$^2$, about 10 mg/m$^2$ to about 20 mg/m$^2$, about 15 mg/m$^2$ to about 25 mg/m$^2$, about 0.5 mg/m$^2$ to about 10 mg/m$^2$, or from about 5 mg/m$^2$ to about 12 mg/m$^2$ based on the body surface area of the mammal. Alternatively, a flat dose may be administered, whose amount may range from 5 mg/dose to about 100 mg/dose, about 5 mg/dose to 50 mg/dose, about 10 mg/dose to 60 mg/dose, about 15 mg/dose to about 45 mg/dose, about 50 mg/dose to about 100 mg/dose, about 20 mg/dose to about 70 mg/dose, about 30 mg/dose to about 75 mg/dose, about 25 mg/dose to about 50 mg/dose, or any dose in between or bounded by these ranges. Some dose ranges for a flat dose to be administered by subcutaneous injection can be 5 mg/dose to about 25 mg/dose, 25 mg/dose to about 50 mg/dose, about 15 mg/dose to about 30 mg/dose, about 45 mg/dose to about 70 mg/dose, about 60 mg/dose to about 80 mg/dose, about 1 mg/dose to about 20 mg/dose, about 30 mg/dose to about 60 mg/dose, or about 50 mg/dose to about 100 mg/dose. The chosen dose may be administered repeatedly, particularly for chronic conditions, or the amount per dose may be increased or decreased as treatment progresses. The chosen dose may be administered one or more times per week, monthly, every two months, every three months, every six months, or every year.

For pediatric patients (ages 4-17), a suitable regimen involves the subcutaneous injection of 0.4 mg/kg, up to a maximum dose of 25 mg or more, about 0.1 mg/kg to about 10 mg/kg, about 5 mg/kg to about 15 mg/kg, about 10 mg/kg to about 25 mg/kg, about 10 mg/kg to about 17 mg/kg, about 12 mg/kg to about 20 mg/kg, about 15 mg/kg to about 25 mg/kg, or about 15 mg/kg to about 40 mg/kg, to be administered one or more times per week, monthly, every two months, every three months, every six months, or every year. If an antibody against RANK or RANKL is used as the RANK/RANKL antagonist, useful dose ranges include about 0.1 mg/kg to about 20 mg/kg, about 0.75 mg/kg to about 7.5 mg/kg and about 1 mg/kg to about 10 mg/kg of body weight. The chosen dose may be administered repeatedly, particularly for chronic conditions, or the amount per dose may be increased or decreased as treatment progresses. The chosen dose may be administered one or more times per week, monthly, every two months, every three months, every six months, or every year.

Useful doses for an antibody against RANK or RANKL, such as denosumab, may range from about 0.1 mg/kg to about 20 mg/kg, about 0.75 mg/kg to about 7.5 mg/kg, about 0.1 mg/kg to about 5 mg/kg, about 1 mg/kg to about 2 mg/kg, about 10 mg/kg to about 20 mg/kg, about 12 to about 17 mg/kg, about 15 mg/kg to about 20 mg/kg, about 1 mg/kg, about 1 mg/kg to about 10 mg/kg, or any value bounded by or in between these ranges based on the body weight of the mammal. The chosen dose may be administered repeatedly, particularly for chronic conditions, or the amount per dose may be increased or decreased as treatment progresses. The chosen dose may be administered one or more times per week, monthly, every two months, every three months, every six months, or every year.

Doses of the antagonist may be administered daily, weekly, monthly, every three months, every six months, or every year. Doses may be administered in single or divided doses. In some embodiments, humanized antibodies are used, that is, antibodies in which only the antigen-binding portion of the antibody molecule is derived from a non-human source. Antibodies may be administered by injection, including intravenous infusion. Appropriate dosages can be determined in trials. The amount and frequency of administration will depend, of course, on such factors as the nature and severity of the indication being treated, the desired response, the condition of the patient, and so forth.

Ibrutinub may be administered orally in a therapeutically effective amount, such as about 1 mg to about 1000 mg, about 1 mg to about 500 mg, about 1 mg to 100 mg, about 1 mg to about 10 mg, 20 mg to about 30 mg, 30 mg to about 40 mg, 40 mg to about 50 mg, 50 mg to about 60 mg, 60 mg to about 70 mg, 70 mg to about 80 mg, 90 mg to about 100 mg, about 100 mg to 1000 mg, about 200 mg to about 700 mg, about 400 mg to about 600 mg, about 560 mg, or about 420 mg. These amounts may be administered daily, weekly, monthly, etc. In some embodiments, ibrutinub may be administered once daily.

In some embodiments the daily dose, such as the daily oral dose, of zoledronic acid or minodronic acid is about 0.005 mg to about 20 mg, about 0.1 mg to about 10 mg, about 0.5 mg to about 10 mg, about 0.2 mg to about 5 mg, about 0.2 mg to about 3 mg, about 0.5 mg to about 5 mg, about 0.5 mg to about 3 mg, about 0.5 mg to about 3 mg, or any amount of zoledronic acid or minodronic acid in a range bounded by, or between, any of these values. In some embodiments, the daily dose, such as the daily oral dose, of zoledronic acid or minodronic acid is less than about 35 mg/m$^2$, less than about 30 mg/m$^2$, less than about 25 mg/m$^2$, about 1 mg/m$^2$ to about 35 mg/m$^2$, about 1 mg/m$^2$ to about 30 mg/m$^2$, about 1.5 mg/m$^2$ to about 25 mg/m$^2$, about 1.8 mg/m$^2$ to about 20 mg/m$^2$, about 10 mg/m$^2$ to about 20 mg/m$^2$, about 10 mg/m$^2$ to about 30 mg/m$^2$, about 15 mg/m$^2$ to about 20 mg/m$^2$, about 18 mg/m$^2$, or any amount of zoledronic acid or minodronic acid in a range bounded by, or between, any of these values.

In some embodiments the weekly dose, such as the weekly oral dose, of zoledronic acid or minodronic acid can be about 1 mg to about 1000 mg, about 1 mg to about 500 mg, about 10 mg to about 250 mg, about 100 mg to about 300 mg, about 10 mg to about 100 mg, about 10 mg to about 80 mg, about 40 mg to about 60 mg, about 10 mg to about 150 mg, about 10 mg to about 100 mg, about 10 mg to about 300 mg, about 20 mg to about 150 mg, or about 30 mg to about 100 mg. In some embodiments, the weekly dose, such as the weekly oral dose, of zoledronic acid or minodronic acid can be less than about 250 mg/m$^2$, less than about 200 mg/m$^2$, less than about 175 mg/m$^2$, about 6 mg/m$^2$ to about 250 mg/m$^2$, about 10 mg/m$^2$ to about 210 mg/m$^2$, about 10 mg/m$^2$ to about 170 mg/m$^2$, about 4 mg/m$^2$ to about 140 mg/m$^2$, about 10 mg/m$^2$ to about 100 mg/m$^2$, about 50 mg/m$^2$ to about 100 mg/m$^2$, about 70 mg/m$^2$ to about 90 mg/m$^2$, about 100 mg/m$^2$ to about 140 mg/m$^2$, about 126 mg/m$^2$, or any amount of zoledronic acid or minodronic acid in a range bounded by, or between, any of these values. The weekly oral dose may be given as a single dose, given once during the week, or may be given in 2, 3, 4, 5, 6, or 7 individual doses during the week. In some embodiments, a weekly dose is given for 4, 5, 6, 7, 8, 9, 10, 11, or 12 consecutive weeks.

In some embodiments, the monthly dose, such as the monthly oral dose, of zoledronic acid or minodronic acid, or the amount of zoledronic acid or minodronic acid that can be administered over a period of a month, is about 5000 mg or less, about 4000 mg or less, about 3000 mg or less, about 2000 mg or less, about 1000 mg or less, about 700 mg or less, about 600 mg or less, about 1 mg to about 4,000 mg, about 1 mg to about 1,000 mg, about 10 mg to about 1000 mg, about 50 mg to about 1000 mg, about 10 mg to about 600 mg, about 10 mg to about 300 mg, about 100 mg to about 300 mg, about 100 mg to about 200 mg, about 200 mg to about 300 mg, about 40 mg to about 600 mg, about 50 mg to about 600 mg, about 200 mg to about 400 mg, or about 100 mg to about 600 mg, about 40 mg to about 2000 mg, about 40 mg to about 800 mg, about 50 mg to about 800 mg, or about 100 mg to about 800 mg, about 40 mg to about 1000 mg, about 50 mg to about 1000 mg, or about 100 mg to about 1000 mg, or any monthly dose in a range bounded by, or between, any of these values.

In some embodiments, the monthly dose, such as the monthly oral dose, of zoledronic acid or minodronic acid can be less than about 1000 mg/m$^2$, less than about 800 mg/m$^2$, less than about 600 mg/m$^2$, about 10 mg/m$^2$ to about 1000 mg/m$^2$, about 50 mg/m$^2$ to about 800 mg/m$^2$, about 70 mg/m$^2$ to about 700 mg/m$^2$, about 100 mg/m$^2$ to about 700 mg/m$^2$, about 100 mg/m$^2$ to about 600 mg/m$^2$, about 50 mg/m$^2$ to about 500 mg/m$^2$, about 200 mg/m$^2$ to about 500 mg/m$^2$, about 100 mg/m$^2$ to about 400 mg/m$^2$, about 200 mg/m$^2$ to about 400 mg/m$^2$, about 50 mg/m$^2$ to about 200 mg/m$^2$, about 300 mg/m$^2$ to about 600 mg/m$^2$, about 450 mg/m$^2$ to about 600 mg/m$^2$, about 300 mg/m$^2$ to about 1000 mg/m$^2$, about 400 mg/m$^2$ to about 1000 mg/m$^2$, about 500 mg/m$^2$ to about 1000 mg/m$^2$, about 400 mg/m$^2$ to about 700 mg/m$^2$, about 500 mg/m$^2$ to about 600 mg/m$^2$, about 540 mg/m$^2$, or any amount of zoledronic acid or minodronic acid in a range bounded by, or between, any of these values.

Minodronic acid may be administered, e.g. intravenously, in a therapeutically effective amount, such as 0.1 mg to about 5 mg, about 0.5 mg to about 2 mg, or about 1 mg, about 1 mg to about 10 mg, about 2 mg to about 6 mg, or about 4 mg, about 0.5 mg to about 60 mg, about 4 mg to about 60 mg, or about 40 mg to about 60 mg. The chosen dose may be administered repeatedly, particularly for chronic conditions, or the amount per dose may be increased or decreased as treatment progresses. The chosen dose may be administered one or more times per week, monthly, every two months, every three months, every six months, or every year. In some embodiments, minodronic acid may be administered in an amount that is about 0.1 mg to about 5 mg, about 0.5 mg to about 2 mg, or about 1 mg per week; about 1 mg to about 10 mg, about 2 mg to about 6 mg, or about 4 mg per month; about 0.5 mg to about 60 mg, about 4 mg to about 60 mg, or about 40 mg to about 60 mg per year.

A monthly dose, such as the monthly oral dose, may be given as a single dose, or as two or more individual doses administered during the month. In some embodiments, the monthly dose, such as the monthly oral dose, can be administered in 1, 2, 3, 4, 5, 6, 7, 8, 9, or 10 individual doses during the month. In some embodiments, the monthly dose, such as the monthly oral dose, can be administered in 2 or 3 weekly doses. In some embodiments, the monthly dose, such as the monthly oral dose, can be administered in 4 or 5 weekly doses. In some embodiments, the monthly dose, such as the monthly oral dose, can be administered in 28 to 31 daily doses. In some embodiments, the monthly dose, such as the monthly oral dose, can be administered in 5 to 10 individual doses during the month. The monthly dose, such as the monthly oral dose, may be administered for only 1 month, or may be repeatedly administered for 2, 3, 4, 5, 6 or more months.

The RANK/RANKL antagonists may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. Injection can be a route of administration that may be used, including parenteral injection. Parenteral injections include subcutaneous injections, intraspinal, intrathecal, intraorbital, intravenous, intrarterial, intramuscular, intrasternal, and infusion techniques. Compositions comprising a RANK/RANKL antagonist can be administered by bolus injection or continuous infusion. Routes of systemic administration that may be used include subcutaneous injection and intravenous drip.

Pharmaceutical compositions suitable for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

With respect to oral administration of zoledronic acid or minodronic acid for the treatment of pain associated with inflammation, arthritis, CRPS, or any other condition recited herein, it may helpful if the mammal or human being to which the zoledronic acid is administered does not eat food or drink beverage, (other than any water required to swallow the oral dosage form) for at least about 1 hour, at least about 2 hours, at least about 4 hours, at least about 6 hours, at least about 8 hours, at least about 10 hours, or at least about 12 hours before the zoledronic acid is administered. It may also be helpful if the mammal or human being to which the zoledronic acid is administered does not eat food or drink beverage for at least about 30 minutes, at least about 1 hour, at least about 2 hours, at least about 3 hours, or at least about 4 hours after the zoledronic acid is administered. In some embodiments, a human being to which the zoledronic acid is administered avoids lying down, or remains upright or sits upright, for at least about 30 minutes or about 1 hour after receiving a dosage form containing zoledronic acid. Avoiding food or beverage before or after oral administration of zoledronic acid can improve the bioavailability of the zoledronic acid.

The effective amount of zoledronic acid or minodronic acid will vary depending on various factors known to the treating physicians, such as the severity of the condition to be treated, route of administration, formulation and dosage forms, and age, weight and response of the individual patients.

RANK/RANKL antagonists and other drugs may be formulated into therapeutic compositions comprising an effective amount of the antagonist.

Some embodiments include a pharmaceutical composition comprising a purified soluble protein having RANK/RANKL antagonistic activity, in conjunction with physiologically acceptable carriers, excipients or diluents. Such carriers may be nontoxic to recipients at the dosages and concentrations employed. Inhibitors of the RANK/RANKL interaction for pharmaceutical compositions can be complexed with polyethylene glycol (PEG), metal ions, or incorporated into polymeric compounds such as polyacetic acid, polyglycolic acid, hydrogels, dextran, etc., or incorporated into liposomes, microemulsions, micelles, unilamellar or multilamellar vesicles, erythrocyte ghosts or spheroblasts.

Protein complexes with PEG can be made using known procedures, such as for example, those described in U.S. Pat. No. 5,849,860, U.S. Pat. No. 5,766,897 or other suitable methods. Suitable lipids for liposomal formulation include, without limitation, monoglycerides, diglycerides, cholesterol, sulfatides, lysolecithin, phospholipids, saponin, bile acids, and the like. Preparation of liposomal formulations is within the level of skill in the art, as disclosed, for example, in U.S. Pat. No. 4,235,871; U.S. Pat. No. 4,501,728; U.S. Pat. No. 4,837,028; U.S. Pat. No. 4,737,323; and U.S. Pat. No. 5,858,397. Such compositions will influence the physical state, solubility, stability, rate of in vivo release, and rate of in vivo clearance, and can be thus chosen according to the intended application, so that the characteristics of the carrier will depend on the selected route of administration.

Ordinarily, the preparation of pharmaceutical compositions comprising a RANK/RANKL antagonist that is a protein entails combining the therapeutic protein with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with conspecific serum albumin can be exemplary appropriate diluents. In certain embodiments, the product can be formulated as a lyophilizate using appropriate excipient solutions (e.g., sterile water or sucrose solution) as diluents. One embodiment entails packaging a lyophilized RANK/RANKL antagonist in dose unit form which when reconstituted will provide one to three doses per package.

In one aspect at least one RANK/RANKL antagonist or a pharmaceutically acceptable salt thereof or composition comprising same can be used in combination with another therapy indicated for pain or other neurological disorders.

Small molecule RANK/RANKL antagonists, including ibrutinib, zoledronic acid, and minodronic acid, may be formulated for oral administration, for example, with an inert diluent or with an edible carrier, or it may be enclosed in hard or soft shell gelatin capsules, compressed into tablets, or incorporated directly with the food of the diet. For oral therapeutic administration, the active compound may be incorporated with an excipient and used in the form of ingestible tablets, buccal tablets, coated tablets, troches, capsules, elixirs, dispersions, suspensions, solutions, syrups, wafers, patches, and the like.

Tablets, troches, pills, capsules and the like may also contain one or more of the following: a binder such as gum tragacanth, *acacia*, corn starch or gelatin; an excipient, such as dicalcium phosphate; a disintegrating agent such as corn starch, potato starch, alginic acid and the like; a lubricant such as magnesium stearate; a sweetening agent such as sucrose, lactose or saccharin; or a flavoring agent such as peppermint, oil of wintergreen or cherry flavoring. When the unit dosage form is a capsule, it may contain, in addition to materials of the above type, a liquid carrier. Various other materials may be present as coating, for instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. It may be desirable for material in a dosage form or pharmaceutical composition to be pharmaceutically pure and substantially non toxic in the amounts employed.

Some compositions or dosage forms may be a liquid, or may comprise a solid phase dispersed in a liquid.

Zoledronic acid may be formulated for parenteral or intraperitoneal administration. Solutions of the active compounds as free acids or pharmacologically acceptable salts can be prepared in water suitably mixed with a surfactant, such as hydroxypropylcellulose. A dispersion can also have an oil dispersed within, or dispersed in, glycerol, liquid polyethylene glycols, and mixtures thereof. Under ordinary conditions of storage and use, these preparations may contain a preservative to prevent the growth of microorganisms.

In some embodiments, sustained-release forms of RANK/RANKL antagonists can be used. Sustained-release forms suitable for use in the disclosed methods include, but are not limited to, soluble RANK polypeptides, and antagonistic anti-RANK or anti-RANKL antibodies that can be encapsulated in a slowly-dissolving biocompatible polymer (such as the alginate microparticles described in U.S. Pat. No. 6,036, 978), admixed with a slow-release polymer (including topically applied hydrogels), and/or incorporated into a biocompatible semi-permeable implant.

The amount of the RANK/RANKL antagonist, such as denosumab, or a small molecule such as ibrutinib, zoledronic acid, or minodronic acid, in a therapeutic composition may vary. For example, some liquid compositions may comprise about 0.0001% (w/v) to about 50% (w/v), about 0.01% (w/v) to about 20% (w/v), about 0.01% to about 10% (w/v), about 0.001% (w/v) to about 1% (w/v), about 0.1% (w/v) to about 0.5% (w/v), about 1% (w/v) to about 3% (w/v), about 3% (w/v) to about 5% (w/v), about 5% (w/v) to about 7% (w/v), about 7% (w/v) to about 10% (w/v), about 10% (w/v) to about 15% (w/v), about 15% (w/v) to about 20% (w/v), about 20% (w/v) to about 30% (w/v), about 30% (w/v) to about 40% (w/v), or about 40% (w/v) to about 50% (w/v) of the RANK/RANKL antagonist.

Some solid compositions may comprise at least about 5% (w/w), at least about 10% (w/w), at least about 20% (w/w), at least about 50% (w/w), at least about 70% (w/w), at least about 80%, about 10% (w/w) to about 30% (w/w), about 10% (w/w) to about 20% (w/w), about 20% (w/w) to about 30% (w/w), about 30% (w/w) to about 50% (w/w), about 30% (w/w) to about 40% (w/w), about 40% (w/w) to about 50% (w/w), about 50% (w/w) to about 80% (w/w), about 50% (w/w) to about 60% (w/w), about 70% (w/w) to about 75% (w/w), about 70% (w/w) to about 80% (w/w), or about 80%

(w/w) to about 90% (w/w) of a RANK/RANKL antagonist such as a ibrutinib, zoledronic acid, or minodronic acid.

Any suitable amount of RANK/RANKL antagonist, such as denosumab, ibrutinib, zoledronic acid, or minodronic acid, may be used. Some solid or liquid oral dosage forms, or units of oral dosage forms (referred to collectively herein as "oral dosage form(s)") may contain about 0.005 mg to about 20 mg, about 0.1 mg to about 10 mg, about 0.5 mg to about 10 mg, about 0.2 mg to about 5 mg, about 1 mg to about 500 mg, about 1 mg to about 50 mg, about 1 mg to about 75 mg, about 10 mg to about 250 mg, about 100 mg to about 300 mg, about 20 mg to about 200 mg, about 20 mg to about 150 mg, about 30 mg to about 100 mg, about 30 mg to about 150 mg, about 1 mg to about 1,000 mg, about 10 mg to about 50 mg, about 10 mg to about 300 mg, about 10 mg to about 150 mg, about 10 mg to about 100 mg, about 40 mg to about 150 mg, about 40 mg to about 220 mg, about 10 mg to about 600 mg, about 40 mg to about 600 mg, about 40 mg to about 2000 mg, about 40 mg to about 800 mg, about 25 mg to about 800 mg, about 30 mg to about 800 mg, about 10 mg to about 500 mg, about 50 mg to about 150 mg, about 50 mg, about 100 mg, about 50 mg to about 500 mg, about 100 mg to about 2000 mg, about 300 mg to about 1500 mg, about 200 mg to about 1000 mg, about 100 mg to about 500 mg, or about 150 mg of zoledronic acid or minodronic acid, or any amount of RANK/RANKL antagonist in a range bounded by, or between, any of these values. In some embodiments, the RANK/RANKL antagonist can be administered daily, weekly, monthly, every two or three months, once a year, or twice a year.

In some embodiments, an oral dosage form may contain about 10 mg/m² to about 20 mg/m², about 15 mg/m² to about 20 mg/m², about 18 mg/m², about 80 mg/m² to about 150 mg/m², about 90 mg/m² to about 150 mg/m², about 100 mg/m² to about 150 mg/m² of zoledronic acid or minodronic acid, or any amount of the compound in a range bounded by, or between, any of these values. All dosage ranges or amounts expressed in mg/m² can be based upon the body surface area of the mammal.

Oral zoledronic acid, or disodium salt thereof, may be administered in combination with about 0.1 mg to about 10 mg of zoledronic acid, or a salt thereof, administered parenterally, such as intravenously. In some embodiments, about 50 mg, about 100 mg, or about 150 mg of the disodium salt of zoledronic acid can be administered orally in combination with 1 mg parenteral, such as intravenous, zoledronic acid. In some embodiments the parenteral dose of zoledronic acid can be about 0.25 mg to about 25 mg, about 0.25 mg to about 10 mg, or about 0.5 mg to about 7.5 mg.

The oral bioavailability of zoledronic acid or minodronic acid may be enhanced by orally administering the zoledronic acid or minodronic acid in the disodium salt form.

For example, the bioavailability of zoledronic acid may be improved by at least about 10%, at least about 20%, at least about 30%, at least about 50%, and/or up to about 100%, or up to about 200%, as compared to administration of zoledronic acid in the diacid form.

Similarly, the bioavailability of minodronic acid may be improved by at least about 10%, at least about 20%, at least about 30%, at least about 50%, and/or up to about 100%, or up to about 200%, as compared to administration of minodronic acid in the diacid form.

Because of the improved bioavailability of the disodium salt a dosage form may contain, or a mammal, such as a human being, may receive, on a molar basis, less of the disodium salt form of zoledronic acid or minodronic acid than would otherwise be administered of the diacid form of zoledronic acid.

For example, a dosage form may contain, or a mammal may receive, at least about 10 mole % less, at least about 20 mole % less, at least about 40 mole % less, at least about 50 mole % less, and/or up to about 90 mole % less or 95 mole % less, of the disodium salt form as compared the amount of the diacid form of zoledronic acid that would otherwise be administered, such as a molar amount that would be administered of zoledronic acid in the diacid form in order to achieve the same plasma levels of zoledronic acid.

Similarly, a dosage form may contain, or a mammal may receive, at least about 10 mole % less, at least about 20 mole % less, at least about 40 mole % less, at least about 50 mole % less, and/or up to about 90 mole % less or 95 mole % less, of the disodium salt form as compared the amount of the diacid form of minodronic acid that would otherwise be administered, such as a molar amount that would be administered of minodronic acid in the diacid form in order to achieve the same plasma levels of minodronic acid.

In some embodiments, a dosage form contains, or a mammal (such as a human being) can be administered, an amount of the disodium salt form, on a molar basis, that has a value of about $0.8\ n_d$ to about $1.2\ n_d$ or about $0.9\ n_d$ to about $1.1\ n_d$, wherein:

$$n_d = (b_a/b_d)(n_a)$$

wherein $b_a$ is the bioavailability of the diacid form, $b_d$ is the bioavailability of the disodium salt form, and $n_a$ is the number of moles of the diacid that would be administered in a dosage form containing the diacid form of zoledronic acid. For example, if the diacid form has a bioavailability ($b_a$) of 0.01 and the disodium salt form has a bioavailabity ($b_d$) of 0.015, and a dosage form would normally contain 0.001 moles of the diacid, $n_d$ would be (0.01/0.015)(0.001 moles), or about 0.00067 moles. In some embodiments, the disodium salt can be administered in an amount that has a value of about $n_d$.

With respect to oral dosage forms comprising a reduced molar amount of the disodium salt of zoledronic acid as compared to the diacid form of zoledronic acid, in some embodiments, the bioavailability of the zoledronic acid in the disodium salt form can be sufficiently high that, if the drug is administered to a mammal, at least as much zoledronic acid is present in the blood of the mammal as would be present if zoledronic acid were administered in the diacid form.

With respect to oral dosage forms comprising the disodium salt form of zoledronic acid, in some embodiments, the disodium salt form can be present in a lower molar amount than would be present if the zoledronic acid were in the diacid form; and the zoledronic acid in the disodium salt form has an improved bioavailability as compared to the zoledronic acid in the diacid form to the extent that the lower molar amount of the disodium salt in the dosage form does not reduce the amount of zoledronic acid delivered to the plasma of a mammal.

In some embodiments, the zoledronic acid in the disodium salt form can be present in an amount such that the oral dosage form provides an area under the plasma concentration curve of zoledronic acid of about 4 ng·h/mL to about 2000 ng·h/mL to the mammal each time the zoledronic acid in the disodium salt is administered.

In some embodiments, the zoledronic acid in the disodium salt form is present in an amount such that the oral dosage form provides an area under the plasma concentration curve of zoledronic acid of about 100 ng·h/mL to about 2000 ng·h/mL, about 100 ng·h/mL to about 1000 ng·h/mL, about 500 ng·h/mL to about 1000 ng·h/mL, or about 500 ng·h/mL to about 700 ng·h/mL in the mammal to which the dosage form is administered. This amount may be suitable for administration of the oral dosage form about every 3 to 4 weeks.

In some embodiments, the zoledronic acid in the disodium salt form can be present in an amount such that the oral dosage form provides an area under the plasma concentration curve of zoledronic acid of about 20 ng·h/mL to about 700 ng·h/mL, about 50 ng·h/mL to about 500 ng·h/mL, or about 100 ng·h/mL to about 200 ng·h/mL, in the mammal to which the dosage form is administered. This amount may be suitable for weekly administration of the oral dosage, or for administration of 3 to 5 individual dosages during a month. The individual dosages could be given at regular intervals, given during the first week, or at any other schedule that provides 3 to 5 dosages during the month.

In some embodiments, the zoledronic acid in the disodium salt form can be present in an amount such that the oral dosage form provides an area under the plasma concentration curve of zoledronic acid of about 4 ng·h/mL to about 100 ng·h/mL, about 10 ng·h/mL to about 50 ng·h/mL, or about 10 ng·h/mL to about 30 ng·h/mL, in the mammal to which the dosage form is administered. This amount may be suitable for daily administration of the oral dosage form.

Oral administration of zoledronic acid, particularly oral administration of the disodium salt form of zoledronic acid, can result in more sustained plasma levels of the drug as compared to parenteral modes of administration, such intravenous or subcutaneous. For example, the amount of zoledronic acid in the plasma can be significantly higher for oral administration of the disodium salt about 24 hours or 48 hours, or longer, after administration. In some embodiments, oral zoledronic acid has a 24 hour sustained plasma level factor of about 1 or higher, such as about 1 to about 10, about 1 to about 5, about 3 to about 5, or about 3 to about 4. In some embodiments, an orally administered dosage form of zoledronic acid has a 24 hour sustained plasma level factor or a 48 hour sustained plasma level factor that can be higher, such as at least 1.2 times, at least about 2 times, at least about 5 times, about 1.2 times to about 20 times, about 2 times to about 15 times, about 5 times to about 10 times, or about 8 to about 15 times that of intravenously administered zoledronic acid. A "sustained plasma level factor," $p_f$, can be determined by the equation:

$$p_f = 1000(C_t/C_{max})$$

wherein $C_{max}$ is the maximum plasma concentration of zoledronic acid after it is administered and $C_t$ is the plasma concentration of zoledronic acid at the time of interest, such as 24 hours. For parenteral administration, the $C_{max}$ can be about the $C_0$, or the concentration right after injection of the entire amount of the drug into the body. Sustained plasma level factors can also be obtained for other times, such as 48 hours, by using the plasma concentration of zoledronic acid for $C_t$ in the equation above. For example, if the maximum plasma level of zoledronic acid after administration is 1000 ng/mL and the plasma level of zoledronic acid at 24 hours is 1 ng/mL, the 24 hour sustained plasma level factor is 1.

In some embodiments, the disodium salt form of zoledronic acid provides an enhancement to bioavailability, as compared to the diacid form of zoledronic acid, which adds to any enhancement to bioavailability provided by any bioavailability-enhancing agents in the dosage form. In some embodiments, the disodium salt form of zoledronic acid provides an enhancement to bioavailability, as compared to the diacid form of zoledronic acid, which is greater than any enhancement to bioavailability provided by any bioavailability-enhancing agents in the dosage form. In some embodiments, the disodium salt form of zoledronic acid may be administered in a dosage form that is substantially free of bioavailability-enhancing agents.

In some embodiments, a dosage form comprising a disodium salt of zoledronic acid is a solid.

In some embodiments, a dosage form comprising a disodium salt of zoledronic acid can be used to treat an inflammatory condition.

In some embodiments, a dosage form comprising a disodium salt of zoledronic acid can be used to treat arthritis.

In some embodiments, a dosage form comprising a disodium salt of zoledronic acid can be used to treat complex regional pain syndrome.

In some embodiments, zoledronic acid can be in a form that has an aqueous solubility, meaning the solubility in water, greater than 1% (w/v), about 5% (w/v) to about 50% (w/v), about 5% (w/v) to about 20% (w/v), about 10% (w/v) to about 15% (w/v), or about 12% (w/v) to about 13% (w/v).

The disodium salt form of zoledronic acid can be more compressible than the diacid form of zoledronic acid. This can make it easier for a dosage form to have a desired hardness. It can also make it easier to increase the drug load, so that a smaller tablet can be given for a given dosage strength. In some embodiments, a solid dosage form of zoledronic acid, such as the diacid form of zoledronic acid or the disodium salt form of zoledronic acid, can have a hardness of about 5 kPa to about 20 kPa or about 5 kPa to about 14 kPa.

The oral bioavailability of zoledronic acid in a dosage form can vary. Some dosage forms may have ingredients added to enhance the bioavailability. However, bioavailability enhancement might not be necessary for an oral dosage form to be effective. In some embodiments, the dosage form can be substantially free of bioavailability-enhancing agents. In some embodiments, an oral dosage form may have an oral bioavailability of zoledronic acid of about 0.01% to about 10%, about 0.1% to about 7%, about 0.1% to about 5%, etc. Without ingredients or other methods to enhance bioavailability, zoledronic acid typically has a low bioavailability in an oral dosage form. In some embodiments, the oral bioavailability of zoledronic acid can be unenhanced or substantially unenhanced. For example, the oral bioavailability of zoledronic acid can be about 0.01% to about 5%, about 0.01% to about 4%, about 0.1% to about 3%, about 0.1% to about 2%, about 0.2% to about 2%, about 0.2% to about 1.5%, about 0.3% to about 1.5%, about 0.3% to about 1%, about 0.1% to about 0.5%, about 0.3% to about 0.5%, about 0.5% to about 1%, about 0.6% to about 0.7%, about 0.7% to about 0.8%, about 0.8% to about 0.9%, about 0.9% to about 1% to about 1.1%, about 1.1% to about 1.2%, about 1.2% to about 1.3%, about 1.3% to about 1.4%, about 1.4% to about 1.5%, about 1.5% to about 1.6%, about 1.6% to about 1.8%, or about 1.8% to about 2%.

One embodiment is a pharmaceutical composition comprising zoledronic acid wherein the oral bioavailability of zoledronic acid in the dosage form is from about 0.01% to about 10%, about 0.01% to about 5%, about 0.1% to about 7%, about 0.1% to about 5%, about 0.1% to about 3%, about 0.1% to about 2%, about 0.2% to about 2%, about 0.2% to about 1.5%, about 0.3% to about 1.5%, about 0.3% to about 1.0%, about 1% to about 2.5%, about 1.2% to about 2.5%, about 1.5% to about 2.5%, about 1% to about 2.7%, about 1.2% to about 2.7%, about 1.5% to about 2.7%, about 1% to about 3%, about 1.2% to about 3%, about 1.5% to about 3%, about 1% to about 3.5%, about 1.2% to about 3.5%, about 1.5% to about 3.5%.

An oral dosage form comprising zoledronic acid or minodronic acid may be included in a pharmaceutical product comprising more than one unit of the oral dosage form.

In some embodiments, an oral dosage form comprises about 10 mg to about 300 mg of zoledronic acid, and can be administered daily for about 2 to about 15 consecutive days. This regimen may be repeated once monthly, once every two months, once every three months, once every four months, once every five months, once every six months, once yearly, or once every two years.

In some embodiments, an oral dosage form comprises about 10 mg to about 150 mg or about 10 mg to about 100 mg of zoledronic acid, and can be administered daily for about 2 to about 15 consecutive days. This regimen may be repeated once monthly, once every two months, once every three months, once every four months, once every five months, once every six months, once yearly, or once every two years.

In some embodiments, an oral dosage form comprises about 10 mg to about 150 mg or about 10 mg to about 100 mg of zoledronic acid, and can be administered daily for about 5 to about 10 consecutive days. This regimen may be repeated once monthly, once every two months, once every three months, once every four months, once every five months, once every six months, once yearly, or once every two years.

In some embodiments, an oral dosage form comprises about 40 mg to about 150 mg of zoledronic acid, and can be administered daily for about 5 to about 10 consecutive days. This regimen may be repeated once monthly, once every two months, once every three months, once every four months, once every five months, once every six months, once yearly, or once every two years.

In some embodiments, the oral zoledronic acid may be administered as one dose of about 100 mg to about 2000 mg. In some embodiments, the oral zoledronic acid may be administered as one dose of about 300 mg to about 1500 mg. In some embodiments, the oral zoledronic acid may be administered as one dose of about 200 mg to about 1000 mg. The dose of zoledronic acid may be administered in a single or divided dose.

A pharmaceutical product containing oral dosage forms for daily use can contain 28, 29, 30, or 31 units of the oral dosage form for a monthly supply. An approximately 6 week daily supply can contain 40 to 45 units of the oral dosage form. An approximately 3 month daily supply can contain 85 to 95 units of the oral dosage form. An approximately six-month daily supply can contain 170 to 200 units of the oral dosage form. An approximately one year daily supply can contain 350 to 380 units of the oral dosage form.

A pharmaceutical product containing oral dosage forms for weekly use can contain 4 or 5 units of the oral dosage form for a monthly supply. An approximately 2 month weekly supply can contain 8 or 9 units of the oral dosage form. An approximately 6 week weekly supply can contain about 6 units of the oral dosage form. An approximately 3 month weekly supply can contain 12, 13 or 14 units of the oral dosage form. An approximately six-month weekly supply can contain 22 to 30 units of the oral dosage form. An approximately one year weekly supply can contain 45 to 60 units of the oral dosage form.

A pharmaceutical product may accommodate other dosing regimes. For example, a pharmaceutical product may comprise 5 to 10 units of the oral dosage form, wherein each unit of the oral dosage form contains about 40 mg to about 150 mg of zoledronic acid. Some pharmaceutical products may comprise 1 to 10 units of the oral dosage form, wherein the product contains about 200 mg to about 2000 mg of zoledronic acid. For such a product, each unit of the oral dosage form may be taken daily for 1 to 10 days or 5 to 10 days during a month, such as at the beginning of a month.

Some oral dosage forms comprising zoledronic acid or a salt thereof may have enteric coatings or film coatings.

In the examples below, zoledronic acid was used to produce RANK/RANKL antagonism.

EXAMPLES

Example 1

Effect of RANK/RANKL Antagonism in Rat Model of Inflammatory Pain Method

Inflammatory pain was induced by injection of 100% CFA in a 75 µL volume into the left hind paws of Sprague-Dawley rats on day 0, followed by assessments on days 1-4. Animals were orally administered zoledronic acid 3 mg/kg (or 18 mg/m$^2$) to produce RANK/RANKL antagonism, or vehicle (control). Drug was dissolved in distilled water and prepared fresh daily. Animals were fasted prior to dosing.

Values for inflammatory pain (mechanical hyperalgesia) in the vehicle and drug-treated animals were obtained on day 0 prior to CFA injection, and at baseline and post-treatment on days 1-4. Pain was assessed using a digital Randall-Selitto device (dRS; IITC Life Sciences, Woodland Hills, Calif.). Animals were placed in a restraint sling that suspended the animal, leaving the hind limbs available for testing. Paw compression threshold was measured by applying increasing pressure to the plantar surface of the hind paw with a dome-shaped tip placed between the 3rd and 4th metatarsus. Pressure was applied gradually over approximately 10 seconds. Measurements were taken from the first observed nocifensive behavior of vocalization, struggle or withdrawal. A cut-off value of 300 g was used to prevent injury to the animal.

Reversal of inflammatory pain was calculated according to the formula:

$$\% \text{ reversal} = (\text{Post-treatment} - \text{Post-CFA baseline})/(\text{Pre-CFA baseline} - \text{Post-CFA baseline}) \times 100.$$

Total Pain Relief (TOTPAR), for the 24 hours following vehicle or drug administration, was calculated as the area under the pain relief (reversal of inflammatory pain) versus time curve, as described in US 2014/0107210, using the linear trapezoidal rule. Values for total pain relief were quantified as %·hr, or the product of reversal of inflammatory pain (%) and time (hr).

The experiment was carried out using 9-10 animals per group.

Results:

RANK/RANKL antagonism with zoledronic acid significantly improved inflammatory pain thresholds compared to vehicle. Pain threshold measurements taken at various times are shown in FIG. 1. Paw compression thresholds were higher than for vehicle during the entire measurement period after 30 minutes from the start of treatment.

Figure 2:
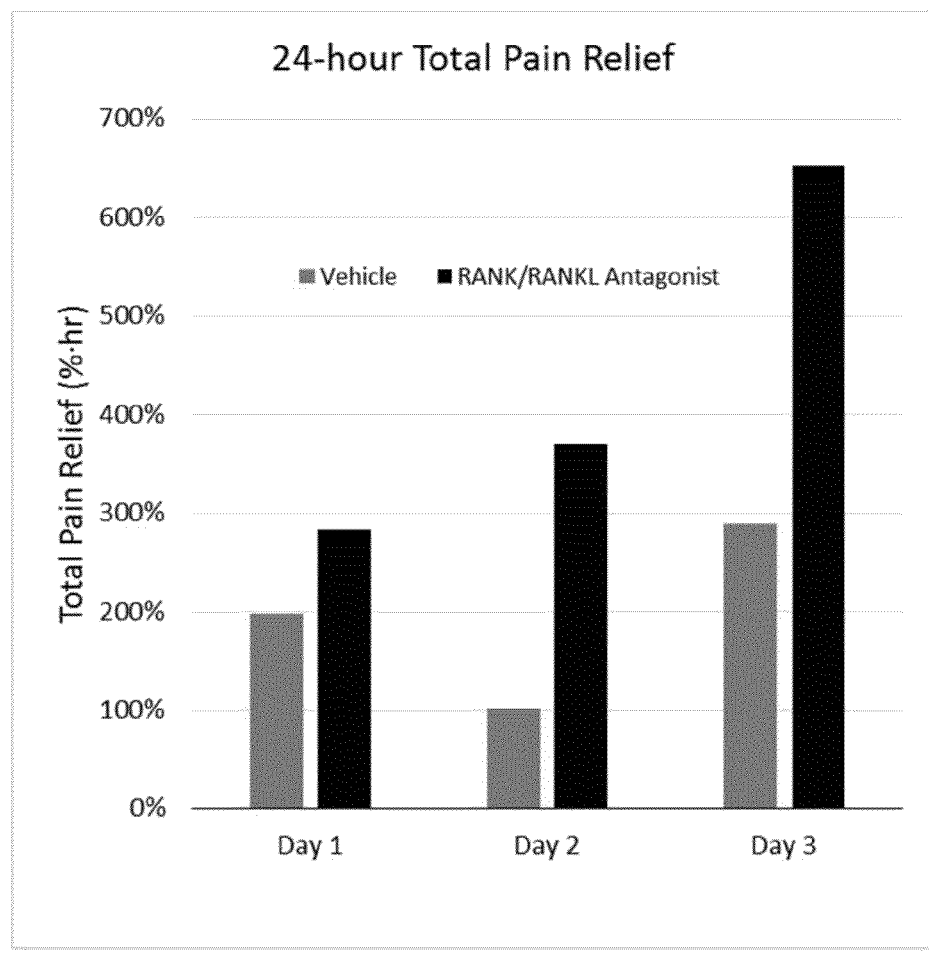
FIG. 2 illustrates the Total Pain Relief over time for rats treated with vehicle or RANK/RANKL antagonism in a rat model of inflammatory pain.

RANK/RANKL antagonism resulted in greater 24-hour Total Pain Relief than that achieved with vehicle treatment on all dosing days as shown in FIG. 2.

Example 2

Effect of RANK/RANKL Antagonism in Rat Model of Arthritis Pain Method

The effect of RANK/RANKL antagonism on arthritis pain was examined in the rat complete Freund's adjuvant (CFA) model of arthritis pain. In this model, injection of 100% complete Freund's adjuvant (CFA) in a 75 µL volume into the left hind paws is followed by a 10-14 day period to allow for the development of arthritis pain. Animals were orally administered zoledronic acid 9 mg/kg (or 54 mg/m$^2$), or zoledronic acid 60 mg/kg (or 360 mg/m$^2$) to produce RANK/RANKL antagonism, divided in three equal daily doses on the first three days post CFA injection, or vehicle (control). Drug was dissolved in distilled water and prepared fresh daily. Animals were fasted prior to dosing.

Arthritis pain (mechanical hyperalgesia) in the vehicle and drug-treated animals was evaluated on day 14 post CFA injection using a digital Randall-Selitto device (dRS; IITC Life Sciences, Woodland Hills, Calif.). Animals were placed in a restraint sling that suspended the animal, leaving the hind limbs available for testing. Paw compression threshold was measured by applying increasing pressure to the plantar surface of the hind paw with a dome-shaped tip placed between the 3rd and 4th metatarsus. Pressure was applied gradually over approximately 10 seconds. Measurements were taken from the first observed nocifensive behavior of vocalization, struggle or withdrawal. A cut-off value of 300 g was used to prevent injury to the animal.

Reversal of arthritis pain in the ipsilateral (CFA-injected) paw was calculated according to the formula:

% reversal=(ipsilateral drug threshold−ipsilateral vehicle threshold)/(contralateral vehicle threshold−ipsilateral vehicle threshold)×100.

The experiment was carried out using 7-10 animals per group.

Results

Figure 3:
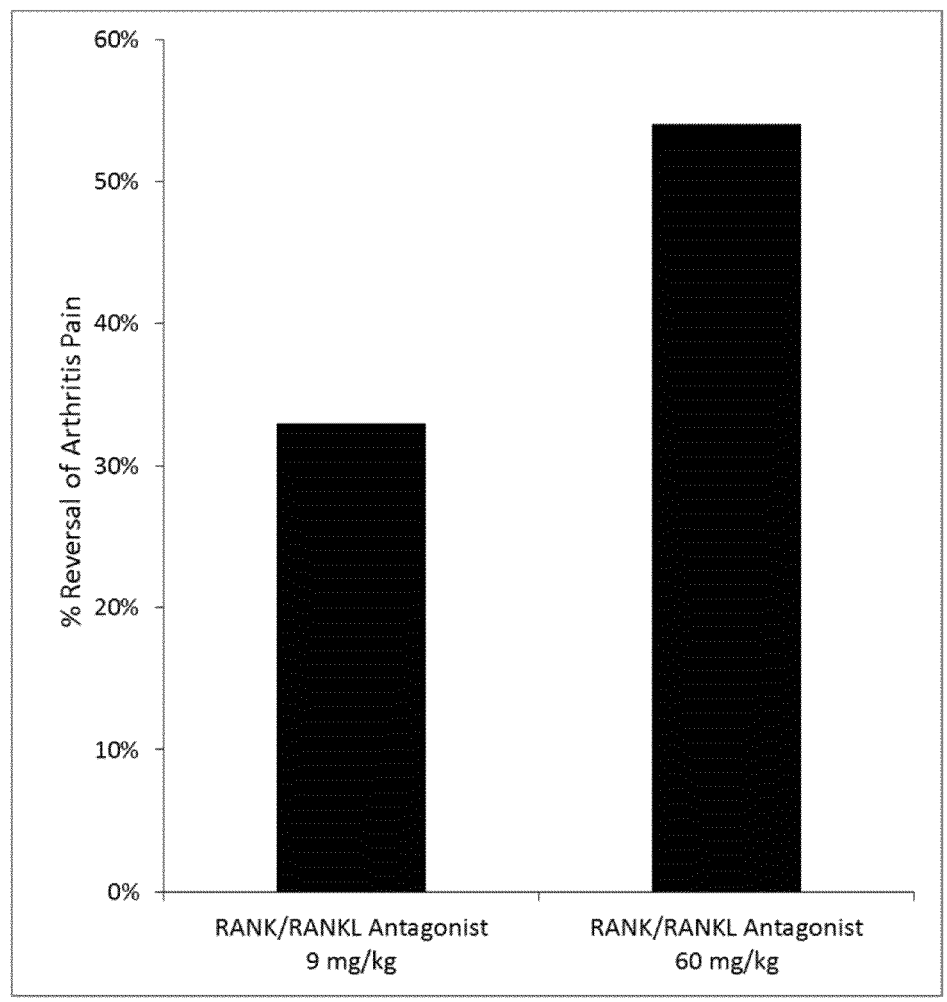
FIG. 3 illustrates the percent reversal of arthritis pain with different doses of RANK/RANKL antagonism in a rat model of arthritis pain.
Figure 4:
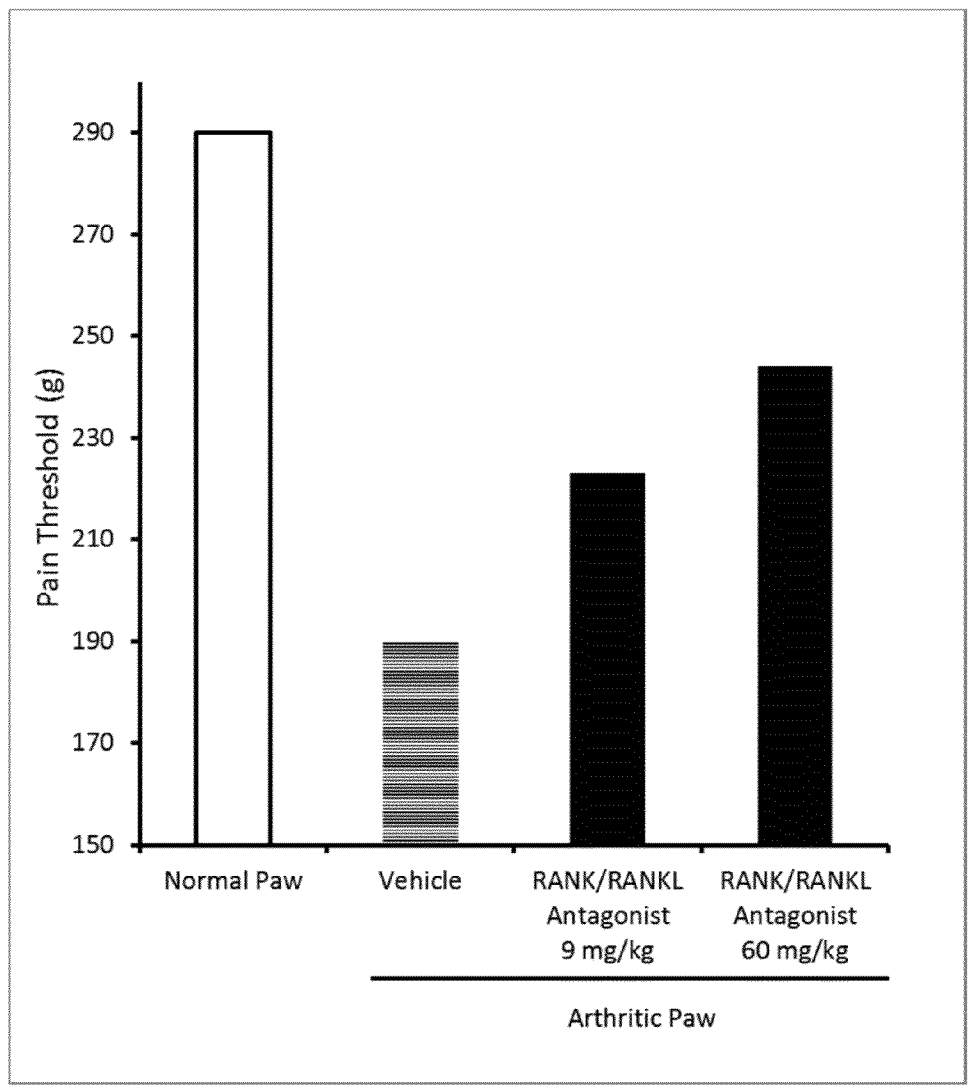
FIG. 4 depicts the mean pain threshold of rats treated with vehicle or RANK/RANKL antagonism in a rat model of arthritis pain.

RANK/RANKL antagonism with zoledronic acid significantly improved arthritis pain thresholds compared to vehicle. As shown in FIGS. 3 and 4, RANK/RANKL antagonism produced a dose-dependent reversal of arthritis pain. A reversal of 33% was observed in the 9 mg/kg group, and reversal of 54% was observed in the 60 mg/kg group.

Example 3

Effect of RANK/RANKL Antagonism in Complex Regional Pain Syndrome (CRPS)

The effect of RANK/RANKL antagonism was examined in the rat tibia fracture model of complex regional pain syndrome (CRPS). CRPS was induced in the rats by fracturing the right distal tibias of the animals and casting the fractured hindpaws for 4 weeks, as described in Guo T Z et al. (Pain. 2004; 108:95-107). This animal model has been shown to replicate the inciting trauma, natural history, signs, symptoms, and pathologic changes observed in human CRPS patients (Kingery W S et al., Pain. 2003; 104:75-84).

The casts were removed on the 28th day after fracture. Starting on day 29, animals were orally administered either zoledronic acid to produce RANK/RANKL antagonism, or vehicle, for 3 weeks. Drug treated animals received zoledronic acid at a dose of 21 mg/kg (126 mg/m$^2$) on the first day (day 29), followed by 3 mg/kg/day (18 mg/m$^2$/day) thereafter. Drug was dissolved in distilled water and administered by gavage. Animals were fasted for 4 hours before and 2 hours after dosing. Bilateral testing of hindpaw pain was performed at baseline, on day 29 after fracture, and then weekly for three weeks.

To measure pain (hyperalgesia), an up-down von Frey testing paradigm was used. Rats were placed in a clear plastic cylinder (20 cm in diameter) with a wire mesh bottom and allowed to acclimate for 15 minutes. The paw was tested with one of a series of eight von Frey hairs ranging in stiffness from 0.41 g to 15.14 g. The von Frey hair was applied against the hindpaw plantar skin at approximately midsole, taking care to avoid the tori pads. The fiber was pushed until it slightly bowed and then it was jiggled in that position for 6 seconds. Stimuli were presented at an interval of several seconds. Hindpaw withdrawal from the fiber was considered a positive response. The initial fiber presentation was 2.1 g and the fibers were presented according to the up-down method of Dixon to generate six responses in the immediate vicinity of the 50% threshold. Stimuli were presented at an interval of several seconds.

Reversal of CRPS pain in the fracture hindpaw was calculated according to the formula:

% reversal=(change in pain threshold from baseline to 4 weeks post-fracture−change in pain threshold from baseline to timepoint after treatment start)/(change in pain threshold from baseline to 4 weeks post-fracture)×100.

Figure 5:
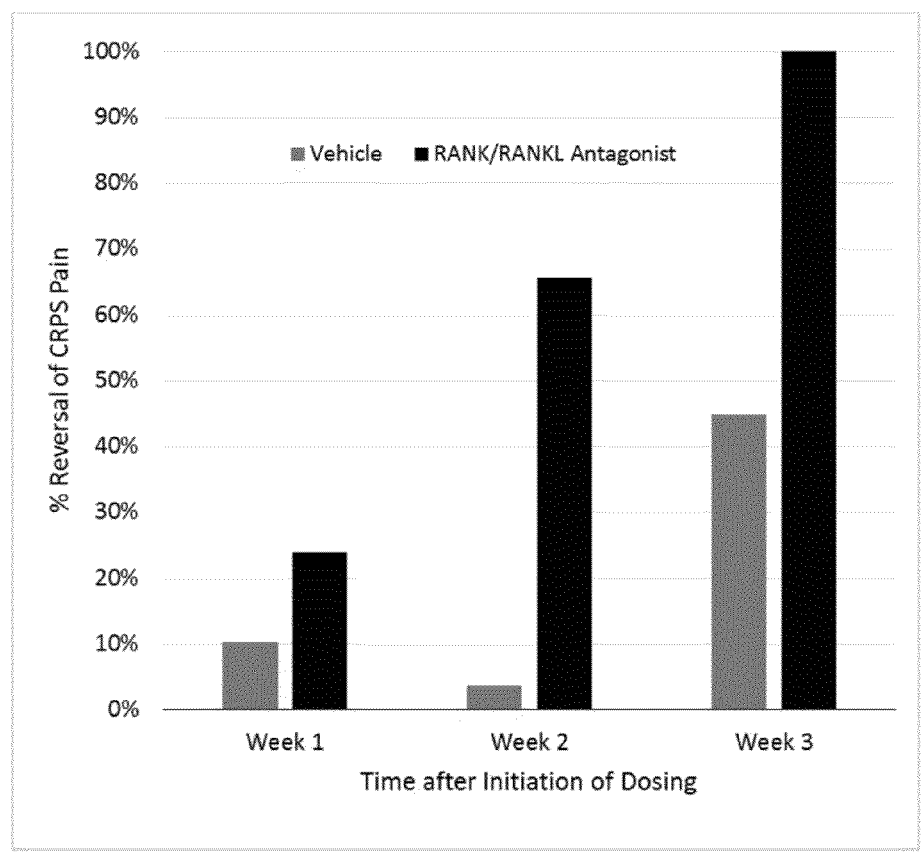
FIG. 5 illustrates the reversal of CRPS pain with RANK/RANKL antagonism.

The experiment was carried out in 6 animals per group. As illustrated in FIG. 5, RANK/RANKL antagonism with zoledronic acid significantly reversed CRPS pain as compared to vehicle treatment. Three weeks after dosing RANK/RANKL antagonism resulted in a complete reversal of CRPS pain.

Example 4

Prolia® (denosumab, 60 mg) is administered subcutaneously to a female patient suffering from complex regional pain syndrome. Within 6 months after receiving the treatment, the patient experiences less pain. The injection is repeated every six months.

Example 5

Prolia® (denosumab, 60 mg) is administered subcutaneously to a male patient suffering from pain associated with arthritis. Within 6 months after receiving the treatment, the patient experiences less pain. The injection is repeated every six months.

Example 6

Prolia® (denosumab, 60 mg) is administered subcutaneously to a male patient suffering from low back pain. Within 6 months after receiving the treatment, the patient experiences less pain. The injection is repeated every six months.

Example 7

Prolia® (denosumab, 60 mg) is administered subcutaneously to a female patient suffering from neuropathic pain. Within 6 months after receiving the treatment, the patient experiences less pain. The injection is repeated every six months.

Example 8

Prolia® (denosumab, 60 mg) is administered subcutaneously to a female patient suffering from pain associated with osteoarthritis. Within 6 months after receiving the treatment, the patient experiences less pain. The injection is repeated every six months.

Example 9

IMBRUVICA® (ibrutinib, 420 mg taken orally once daily (three 140 mg capsules once daily)) is administered to a female patient suffering from complex regional pain syndrome. Within 6 months after beginning treatment, the patient experiences less pain.

Example 10

IMBRUVICA® (ibrutinib, 420 mg taken orally once daily (three 140 mg capsules once daily)) is administered to a male patient suffering from pain associated with arthritis. Within 6 months after beginning treatment, the patient experiences less pain.

Example 11

IMBRUVICA® (ibrutinib, 420 mg taken orally once daily (three 140 mg capsules once daily)) is administered to a male patient suffering from low back pain. Within 6 months after beginning treatment, the patient experiences less pain.

Example 12

IMBRUVICA® (ibrutinib, 420 mg taken orally once daily (three 140 mg capsules once daily)) is administered to a female patient suffering from neuropathic pain. Within 6 months after beginning treatment, the patient experiences less pain.

Example 13

IMBRUVICA® (ibrutinib, 420 mg taken orally once daily (three 140 mg capsules once daily)) is administered to a female patient suffering from pain associated with osteoarthritis. Within 6 months after beginning treatment, the patient experiences less pain.

Example 14

IMBRUVICA® (ibrutinib, 560 mg taken orally once daily, (four 140 mg capsules once daily)) is administered to a female patient suffering from complex regional pain syndrome. Within 6 months after beginning treatment, the patient experiences less pain.

Example 15

IMBRUVICA® (ibrutinib, 560 mg taken orally once daily, (four 140 mg capsules once daily)) is administered to a male patient suffering from pain associated with arthritis. Within 6 months after beginning treatment, the patient experiences less pain.

Example 16

IMBRUVICA® (ibrutinib, 560 mg taken orally once daily, (four 140 mg capsules once daily)) is administered to a male patient suffering from low back pain. Within 6 months after beginning treatment, the patient experiences less pain.

Example 17

IMBRUVICA® (ibrutinib, 560 mg taken orally once daily, (four 140 mg capsules once daily)) is administered to a female patient suffering from neuropathic pain. Within 6 months after beginning treatment, the patient experiences less pain.

Example 18

IMBRUVICA® (ibrutinib, 560 mg taken orally once daily, (four 140 mg capsules once daily)) is administered to a female patient suffering from pain associated with osteoarthritis. Within 6 months after beginning treatment, the patient experiences less pain.

The invention claimed is:

1. A method of treating pain comprising administering a polypeptide or a protein to relieve pain in a mammal in need thereof, wherein the polypeptide or the protein is a RANK/RANKL antagonist, wherein the pain is osteoarthritis pain and the RANK/RANKL antagonist is denosumab.

2. The method of claim 1, wherein, within a period of about six months, about 0.1 mg/kg to about 20 mg/kg of denosumab is administered to the mammal.

3. The method of claim 1, wherein, within a period of about six months, about 0.5 mg/kg to about 2 mg/kg of denosumab is administered to the mammal.

4. The method of claim 3, wherein the denosumab is administered once every six months.

5. The method of claim 1, wherein the mammal is a human being.

6. The method of claim 1, wherein the pain is associated with osteoarthritis of the knee.

7. The method of claim 1, wherein the osteoarthritis affects a knee or hip.

8. The method of claim 1, wherein the osteoarthritis affects an elbow, a shoulder, a wrist, or a finger.

9. A method of treating pain comprising administering a polypeptide or a protein to relieve pain in a mammal in need thereof, wherein the polypeptide or the protein is a RANK/RANKL antagonist, wherein the pain is complex regional pain syndrome and the RANK/RANKL antagonist is denosumab.

10. The method of claim 9, wherein, within a period of about six months, about 0.1 mg/kg to about 20 mg/kg of denosumab is administered to the mammal.

11. The method of claim 9, wherein, within a period of about six months, about 0.5 mg/kg to about 2 mg/kg of denosumab is administered to the mammal.

12. The method of claim 11, wherein the denosumab is administered once every six months.

13. The method of claim 9, wherein the mammal is a human being.

14. A method of treating pain comprising administering a polypeptide or a protein to relieve pain in a mammal in need thereof, wherein the polypeptide or the protein is a RANK/RANKL antagonist, wherein the pain is low back pain and the RANK/RANKL antagonist is denosumab.

15. The method of claim 14, wherein the pain is chronic low back pain.

16. The method of claim 14, wherein the low back pain is associated with Modic changes.

17. The method of claim 14, wherein, within a period of about six months, about 0.1 mg/kg to about 20 mg/kg of denosumab is administered to the mammal.

18. The method of claim 14, wherein, within a period of about six months, about 0.5 mg/kg to about 2 mg/kg of denosumab is administered to the mammal.

19. The method of claim 18, wherein the denosumab is administered once every six months.

20. The method of claim 14, wherein the mammal is a human being.

* * * * *

UNITED STATES PATENT AND TRADEMARK OFFICE
CERTIFICATE OF CORRECTION

| | | |
|---|---|---|
| PATENT NO. | : 9,127,069 B1 | Page 1 of 1 |
| APPLICATION NO. | : 14/495732 | |
| DATED | : September 8, 2015 | |
| INVENTOR(S) | : Herriot Tabuteau | |

It is certified that error appears in the above-identified patent and that said Letters Patent is hereby corrected as shown below:

On the title page, items (71) and (73) should appear as follows:

(71) Applicant: "Antecip Bioventures LLC" should read --Antecip Bioventures II LLC--

(73) Assignee: "Antecip Bioventures LLC" should read --Antecip Bioventures II LLC--

Signed and Sealed this
Sixteenth Day of February, 2016

Michelle K. Lee
*Director of the United States Patent and Trademark Office*

UNITED STATES PATENT AND TRADEMARK OFFICE
CERTIFICATE OF CORRECTION

Page 1 of 1

PATENT NO. : 9,127,069 B1
APPLICATION NO. : 14/495732
DATED : September 8, 2015
INVENTOR(S) : Herriot Tabuteau It is certified that error appears in the above-identified patent and that said Letters Patent is hereby corrected as shown below:

"On the title page, items (71) and (73) should appear as follows:

(71) Applicant: "Antecip Bioventures LLC" should read --Antecip Bioventures II LLC--

(73) Assignee: "Antecip Bioventures LLC" should read --Antecip Bioventures II LLC--"

(as corrected to read in the Certificate of Correction issued February 16, 2016) is deleted and patent is returned to its original state with the applicant & assignee name in patent to read --Antecip Bioventures LLC, New York, NY (US)--

Signed and Sealed this
Thirty-first Day of May, 2016

Michelle K. Lee
*Director of the United States Patent and Trademark Office*

UNITED STATES PATENT AND TRADEMARK OFFICE
CERTIFICATE OF CORRECTION

PATENT NO.        : 9,127,069 B1
APPLICATION NO.   : 14/495732
DATED             : September 8, 2015
INVENTOR(S)       : Herriot Tabuteau Page 1 of 1

It is certified that error appears in the above-identified patent and that said Letters Patent is hereby corrected as shown below:

On the title page:

In the abstract:

Item (57), line 1, "are method of" should read --are methods of--

In the specification:

In column 13, line 52, "arthropaties" should read --arthropathies--

In column 14, line 3, "75 years old," should read --75 years,--

In column 17, line 17, "predisone," should read --prednisone--

In column 24, line 32, "bioavailabity" should read --bioavailability--

In column 28, line 14, "Sprague-Dawley" should read --SPRAGUE-DAWLEY--

Signed and Sealed this
Ninth Day of August, 2016

Michelle K. Lee
*Director of the United States Patent and Trademark Office*